(12) United States Patent
Prince

(10) Patent No.: US 9,844,432 B2
(45) Date of Patent: Dec. 19, 2017

(54) DENTAL FLOSSING DEVICE

(71) Applicant: Victor Prince, Beaverton, OR (US)

(72) Inventor: Victor Prince, Beaverton, OR (US)

( * ) Notice: Subject to any disclaimer, the term of this patent is extended or adjusted under 35 U.S.C. 154(b) by 52 days.

(21) Appl. No.: 14/593,897

(22) Filed: Jan. 9, 2015

(65) Prior Publication Data

US 2016/0199164 A1 Jul. 14, 2016

(51) Int. Cl.
*A61C 15/00* (2006.01)
*A61C 15/04* (2006.01)

(52) U.S. Cl.
CPC ............ *A61C 15/046* (2013.01); *A61C 15/00* (2013.01); *A61C 15/047* (2013.01); *A61C 15/048* (2013.01)

(58) Field of Classification Search
CPC ....... A61C 15/00; A61C 15/046; A61C 15/04; A61C 15/041; A61C 15/047
See application file for complete search history.

(56) References Cited

U.S. PATENT DOCUMENTS

| | | | | |
|---|---|---|---|---|
| 3,696,821 | A * | 10/1972 | Adams, IV | A61C 15/046 |
| | | | | 132/324 |
| 3,745,788 | A * | 7/1973 | Sullivan | A44C 9/02 |
| | | | | 63/15.6 |
| 3,901,251 | A * | 8/1975 | Johnston | A61C 15/046 |
| | | | | 132/325 |
| 4,638,824 | A * | 1/1987 | De La Hoz | A61C 15/046 |
| | | | | 132/323 |
| 5,423,338 | A * | 6/1995 | Hodge | A61C 15/046 |
| | | | | 132/324 |
| 5,435,330 | A | 7/1995 | Dix | |
| 5,454,386 | A | 10/1995 | Dix | |
| 5,477,871 | A | 12/1995 | Sanchez | |
| 5,680,875 | A | 10/1997 | Winters | |
| 5,893,379 | A * | 4/1999 | Ghamaty-Azimi | A61C 15/046 |
| | | | | 132/323 |
| 7,146,987 | B2 * | 12/2006 | Tse | A61C 15/046 |
| | | | | 132/323 |
| 8,042,556 | B2 | 10/2011 | Bowsher | |
| 2012/0186603 | A1 * | 7/2012 | Hall | A61C 15/046 |
| | | | | 132/323 |

* cited by examiner

*Primary Examiner* — Robyn Doan
(74) *Attorney, Agent, or Firm* — Grady L. White; Potomac Law Group, PLLC

(57) ABSTRACT

A dental flossing device comprising a first body circumscribing a void adapted to receive one or more fingers of a user, an outward-facing surface, opposite from the void, having a first segment comprising at least one pair of cleats arranged to define a circumferential groove for receiving and carrying one or more revolutions of the dental floss formed by wrapping the dental floss along the circumferential groove. A second segment of the outward-facing surface includes a fastener comprising a depression, a crown with a base wall and a niche in the base wall, and a pedestal that connects the base wall of the crown to a floor of the depression. The base wall, niche and the pedestal are configured to provide a space located between the floor of the depression and the base wall to receive and secure a free end of the dental floss. The device permits users to easily hold and manipulate the dental floss into position for flossing, eliminating the problems associated with gripping dental floss directly with the hands.

27 Claims, 22 Drawing Sheets

DENTAL FLOSSING DEVICE

CROSS-REFERENCE TO RELATED APPLICATIONS

This application is related to U.S. Design application No. 29/514,262, filed on even date herewith, entitled "Dental Flossing Device," U.S. Design application No. 29/514,273, filed on even date herewith, entitled "Dental Flossing Device," and U.S. Design application No. 29/514,268, filed on even date herewith, entitled "Dental Flossing Device," the disclosures of which are hereby incorporated herein in their entireties by this reference.

FIELD OF ART

The present invention relates generally to dental flossing devices and more particularly to dental flossing devices with improved systems for attaching, extending, gripping and advancing the dental floss during flossing operations and improved systems for storing dental floss when the device is not in use.

BACKGROUND OF THE INVENTION

Flossing one's teeth is an activity that is critical for maintaining good dental health and hygiene. While brushing cleans the surface of the teeth, flossing is necessary to clean out the gaps between the teeth, where food and bacteria often gets caught and remain despite vigorous brushing of the front and rear surfaces of the teeth. Leaving food and bacteria in these gaps accelerates plaque build-up, and can lead to cavities, tooth decay, and gum disease. Left untreated, gum disease can lead to other severe health conditions, such as heart disease, diabetes, and a high body mass index. Bacteria caught between teeth also causes bad breath and may detract from the appearance of the teeth. Despite these serious consequences, flossing on regularly basis using the proper flossing tools and techniques is also one of the most difficult personal health habits for people to develop and incorporate into their daily health and grooming routines.

Dental floss was invented in 1815 by Levi Spear Parmly, a New Orleans dentist who advised his patients to use thin thread to clean between their teeth. Johnson and Johnson patented dental floss in 1898. At the time, it was made out of silk. Today, there are two basic types of dental floss: multifilament dental flosses, such as nylon and silk; and monofilament dental floss, which is generally made of some type of rubber, plastic or polytetrafluoroethylene (PTFE). Nylon dental floss, which tends to be a lot cheaper, comes in a large variety of thicknesses and flavors, and can be bought with or without wax. Monofilament dental floss is a newer technology, and because it isn't a fabric like nylon, it resists ripping and tearing. Also, because monofilament flosses are stronger, many people feel that it is easier to use and pull between teeth. The plastic or rubber material in monofilament dental floss also seems to glide easier between the teeth for many people. Both types of dental floss are available in a variety of different flavors, including, for instance, mint, cinnamon, bubblegum, and even bacon. In addition, both types of dental floss are available in different thicknesses, which is important because different people can have significantly different amounts of space between their teeth. Dental tape, which is a wide, flat ribbon of nylon is another type of dental floss that may be obtained in waxed or un-waxed form. Dental tape is typically easier to insert between the teeth than traditional dental floss because it is generally thinner in one dimension.

The American Dental Association (ADA) recommends the following steps to help achieve maximum efficacy during flossing: (1) Break or cut off about an 18-inch length of dental floss; (2) Wind some of the length of dental floss around the middle finger of one hand; (3) Wind the remaining length of dental floss around the middle finger of the opposite hand, and use this finger to take up the dental floss up as it is used and becomes soiled; (4) Hold the dental floss tightly between the thumbs and forefingers and gently insert it between the teeth; (5) Curve the length of dental floss into a "C" shape against the side of the tooth and rub the dental floss gently up and down, keeping it pressed against the tooth; (6) Do not jerk or snap the dental floss; and (7) Repeat these steps for the rest of the teeth and do not neglect to floss behind the teeth in the rear areas of the mouth.

Anyone who has ever flossed using conventional dental floss knows that flossing, even with the ADA-recommended method, can be a difficult, messy and relatively unpleasant experience for some people. Maintaining a good grip on the dental floss while manipulating the dental floss to position fresh sections of dental floss between the teeth requires a substantial amount of time and attention, as well as a considerable amount of manual dexterity to carry out all of the ADA-recommended steps. The dental floss can be very uncomfortable to grip and use in accordance with the ADA-recommended procedure. Specifically, gripping the dental floss by winding it around the fingers can be very cumbersome and even painful for many users. This discomfort may be intensified by the fact that the dental floss must be squeezed tightly between the thumbs and forefingers to hold it in place between the teeth. It is also difficult to adjust or reposition the dental floss to use a different section of the dental floss because repositioning the floss requires unwinding and rewinding the dental floss around the user's fingers. In addition, gripping, repositioning and manipulating dental floss gradually becomes more and more difficult and uncomfortable during a flossing session as the dental floss gets wet with the user's saliva and/or rinsing.

Although there have been many meaningful advances in the materials, thicknesses, flavors and surface treatments for dental floss, there have been very few innovations over the past 200 years directed to making it any easier, cleaner and more comfortable for people to use dental floss on a regular and consistent basis. Flossing forks and flossing picks have been introduced in an attempt to make flossing less of a hassle for people. However, there are a number of significant disadvantages associated with using flossing forks and picks. First, flossing forks and picks generally do not permit users to select from the large variety of the aforementioned types of dental flosses available on the market today. Second, flossing forks and picks are not environmentally friendly because they require users to dispose of several plastic forks or picks with each flossing, contributing to the amount of plastic that ends up in landfills. Third, flossing forks and picks also tend to be much more expensive than dental floss. Most importantly, however, it is impossible to use flossing forks and picks for flossing and still meet the ADA's recommended efficacy standards for proper flossing because the recommended steps cannot be carried out effectively with anything other than a relatively freely moving and flexible length of dental floss that can easily be manipulated by the thumbs and fingers of each hand during flossing. Therefore, flossing forks and flossing picks are considered by the ADA to be ill-suited for proper flossing. Consequently, using dental floss remains the only approved and recommended method for interdental cleaning recommended by the American Dental Association (ADA).

Different users tend to have very different and very personalized techniques of gripping dental floss. Some users use the ADA-recommended method, while still many others grip the dental floss using the palm, hand, middle, ring and pinky fingers. In most cases, the thumbs and forefingers are used to guide, manipulate and position the dental floss while assisting in gripping. Modification of the grip usually does not necessarily impact the efficacy as long as the ADA-recommended steps can be performed. Nevertheless, when a typical eighteen inch strip of dental floss is used for each flossing session, as recommended by the ADA, only a small fraction is actually engaged with the teeth for flossing. The remainder is used solely for effective gripping of the dental floss and to compensate for the inefficient use of fresh sections of dental floss. Thus, due to the excessive amount of dental floss used solely to facilitate gripping the dental floss with the hands and fingers, there is a considerable amount of waste associated with using dental floss in the conventional ADA-approved manner. Another cause of waste is the difficulty in keeping track of used and unused sections of dental floss so that unused sections can be positioned between gaps in the teeth while flossing. Unused sections of the dental floss are frequently overlooked and discarded. As a result, it has been estimated that, out of the approximately 4 million miles of dental floss produced every year, approximately 2 million miles of it is wasted and ends up in landfills. Due to the large amount of dental floss wasted, the average user who flosses on a regular basis ends up purchasing and discarding twice as much dental floss as he or she actually needs.

The aforementioned challenges of flossing are further exacerbated by the overall messiness of the process. Current methods inevitably result in saliva, bacteria and unsightly blood and food particles coming into contact with the user's hands, fingers and palms. Frustratingly, dental floss cannot be rinsed like a toothbrush because the moisture makes it even more difficult to hold and control. As an alternative, many users resort to using a tissue to clean the dental floss which is not as effective as rinsing, and frequently requires that the user unwind the dental floss completely and then rewind it to establish a new grip. Trying to deal with these problems while flossing often just leads to bacteria, food particles and blood from the used sections of dental floss being re-introduced back into the mouth as the used sections are used to floss new areas of the mouth, reducing the overall efficacy of the entire process.

U.S. Pat. No. 5,435,330 to Dix discloses a dental flossing device comprising two ring portions for holding the dental floss. But each ring portion requires using specially formed segments of dental floss. Specifically, each segment of dental floss must include at each end of the segment a locking means comprising an enlarged portion of dental floss designed to engage with and be locked into a corresponding retaining means in the ring portions. U.S. Pat. No. 5,454,386 to Dix requires using a segment of dental floss having closed loops at either end. Therefore, both of Dix's dental flossing devices suffer from a significant disadvantage in that they cannot be used with ordinary, non-special, conventionally formed segments of floss. Moreover, neither one of Dix's dental flossing devices provides a mechanism for storing a supply of extra, unused dental floss on the rings.

U.S. Pat. No. 5,477,871 to Sanchez attempts to address the disadvantages of Dix's dental flossing devices by providing sidewalls with an annular space therebetween for winding and storing extra dental floss, as well as one or more slots in one of the sidewalls to facilitate tying or wedging dental floss thereto. However, Sanchez's flossing device suffers from other significant disadvantages. One disadvantage is that manually tying the floss to the slots in the sidewall is both cumbersome and difficult. Another disadvantage is that wrapping a sufficient amount of floss over the free end of the floss wedged into the slot in the sidewall in order to provide enough friction to retain the floss on the ring during a flossing operation requires dedicating a large amount of floss (relative to the amount actually used for flossing) solely to the function of securing the floss to the ring. The relatively large amount of floss used solely for securing the floss to the ring is therefore wasted and contributes to the large amount of floss that ends up being discarded and sent to landfills.

Accordingly, there is considerable need in the field of dental flossing devices for a dental flossing device that does not require using sections of dental floss having specially formed ends and does not require wrapping multiple loops of extra dental floss around the storage and dispensing ring solely for the purpose of securing the dental floss to the storage and dispensing ring.

SUMMARY OF THE INVENTION

As will be described in more detail below, aspects and embodiments of the present invention address the above-described needs, as well as many of the deficiencies and problems associated with known dental flossing devices, by providing a dental flossing device that makes it extremely easy to grip and control a length of dental floss and carry out the American Dental Association-recommended flossing procedure, even when the dental floss is wet. Further, embodiments of the present invention reduce the mess associated with flossing by minimizing the amount of saliva, bacteria, blood and food particles that come into contact with and stick to the hands and fingers and get re-introduced to other parts of the mouth. Moreover, embodiments of the present invention reduce the amount of wasted dental floss that ends up in landfills each year by minimizing the amount of dental floss used solely for securing the dental floss to the flossing device, thereby making it possible to more efficiently use substantially the entire length of dental floss for engaging with the gaps between the teeth. Further, embodiments of the present invention significantly reduce the amount of bacteria, food particles, and blood reintroduced into the mouth by separating used sections of dental floss from the unused sections, thereby reducing the possibility of inadvertent re-use, and by permitting the used dental floss to be rinsed without impairing the user's grip. In these respects, the flossing device according to the present invention substantially departs from the conventional concepts and designs of the prior art, and provides a dental flossing device that is uniquely well-suited for carrying out the actions recommended by ADA for proper flossing in a most effective manner.

In general, embodiments of the present invention provide a dental flossing device for use with a length of dental floss, the length of dental floss having a free end that will be secured to the device with an improved fastener as will be described in more detail below. The dental flossing device comprises a first body circumscribing a void adapted to receive one or more fingers of a user. The first body, which may comprise, for example, a ring, a spool or a reel, has an outward-facing surface, opposite from the void. The outward-facing surface is divided into at least two different segments. On the first segment of the outward-facing surface is at least one pair of cleats arranged to define between them a circumferential groove for receiving and carrying one or more revolutions of the length of dental floss formed by wrapping the length of dental floss around the first body along the circumferential groove between the pair of cleats. On the second segment of the outward-facing surface is a fastener comprising a depression, a crown with a base wall and a niche in the base wall, and a pedestal that connects the base wall of the crown to a floor of the depression.

The dimensions of the base wall, the niche in the base wall, and the pedestal are configured to provide a space (i.e., a seat) between the floor of the depression and the base wall of the crown, the space being of sufficient size to receive and secure a section of the free end of the dental floss as it is wound in a loop about the pedestal. The end of the dental floss is then passed through and lodged within the niche in the base wall to secure the section of the free end of the dental floss to the fastener. The length of dental floss is then wrapped into the circumferential groove around the perimeter of the outward-facing surface of the first body. Thus, the base wall, the pedestal, the space between the base wall and the pedestal, and the niche cooperate with each other in order to provide a secure attachment of the dental floss to the first body while using a minimal amount of dental floss.

In preferred embodiments, the base wall of the crown and the pedestal connecting the base wall to the floor of the depression are configured to provide a bridge of sufficient height and orientation to provide support for a portion of the revolutions of dental floss carried by the circumferential groove. The bridge permits the portion of the revolutions passing over the fastener to pass over the fastener without being altered or interfered with by the loops around the pedestal. In other words, the revolutions of dental floss carried by the circumferential groove are held by the bridge in a higher orbit (relative to the center of the void) than the loops wrapped about the pedestal, which means the revolutions carried by the circumferential groove do not impede or divert the path of the loops wrapped around the pedestal, and the loops wrapped around the pedestal do not impede or divert the path of the revolutions of dental floss carried by the circumferential groove.

Ideally, but not necessarily, the bottom surface of the base wall (i.e., the surface of the base wall facing the pedestal) has a length or a width dimension that is relatively larger than the length or width dimension of the pedestal so that the relatively larger dimensions of the bottom surface of the base wall (as compared to the dimensions of the pedestal attached to the base wall) provide a physical barrier that aids in holding the loops of dental floss wrapped around the pedestal in place and maintaining physical separation between the loops of dental floss wrapped around the pedestal and the revolutions of extra dental floss wrapped around the circumferential groove. In preferred embodiments, the crown also has a pair of side walls, connected to the base wall of the crown, the sidewalls being arranged to extend outward from the base wall so as to provide lateral support for the one or more revolutions of dental floss carried by the circumferential groove and to prevent the one or more revolutions of dental floss supported by the bridge from slipping over the lateral sides of the base wall. Thus, the sidewalls of the crown aid in keeping the sections of the one or more revolutions of extra dental floss resting on top of the bridge support substantially in line with the sections of the one or more revolutions of the dental floss carried by the circumferential groove. In preferred embodiments, the revolutions carried by the circumferential groove and the loops wrapped around the pedestal do not even come into contact other.

In some embodiments, the pair of cleats on the first segment of the outward-facing surface are roughly parallel to each other, have roughly the same dimensions, and are roughly aligned next to each other along the first section of the outward-facing surface of the first body. In other embodiments, however, the pair of cleats may not be parallel, may have different dimensions from each other, and may be staggered, relative to each other, along the first section of the outward-facing surface of the first body. In addition, some embodiments may include multiple pairs of cleats on the first section of the outward-facing surface of the first body. For example, the first segment of the outward-facing surface of the first body may include at least two pairs of cleats defining the circumferential groove for receiving and carrying the one or more revolutions of dental floss carried by the circumferential groove. In other embodiments, the first segment of the outward-facing surface of the first body may include at least three, four or five pairs of cleats defining the circumferential groove.

With the free end of the length of the dental floss secured to the fastener in the manner described above, and additional sections of the length of dental floss wrapped around the first body to form the one or more revolutions of dental floss lying in the circumferential groove between the pair of cleats, the opposite free end of the length of dental floss may be attached to and wound around a second body, such as a companion ring, reel or spool, in a similar or identical manner, thereby leaving a section in the middle of the length of dental floss extended between the first body and the second body available to be guided by the user's thumb and/or fingers between the gaps in the user's teeth to perform the flossing procedure. In this implementation of the invention, the first body acts as a storage and dispensing element for fresh, unused dental floss, while the second body acts as a take-up and storage element for used dental floss.

Accordingly, some embodiments of the present invention may include a second body circumscribing a second void adapted to receive one or more fingers from the opposite hand of the user, the second body having a second outward-facing surface opposite from the second void, and a second pair of cleats, disposed on the second outward-facing surface of the second body, defining a second circumferential groove on the second body for taking up and carrying portions of said length of dental floss as said portions of said length of dental floss are unwound and removed from the circumferential groove on the first body. The second body may, or may not, be identical or substantially identical to the first body. It will be understood and appreciated by those skilled in the arts of manufacturing and distributing commercial products, however, that significant manufacturing, packaging and shipping benefits might be achieved when the size, shape and features of the two bodies are identical, or substantially identical, and therefore interchangeable. It should also be appreciated that significant usability benefits accrue for users when the two bodies are interchangeable because no exceptions, allowances or special instructions have to be made or given in order to account for bodies with mutually distinct features or to account for the left- or right-handedness of users.

The first body, the second body, or both the first and the second bodies, may be constructed to form any one of a variety of different geometric shapes, so long as the selected shape circumscribes, or partially circumscribes a void adapted to receive the fingers of a user's hand. For example, one or both of the first and second bodies may comprise a ring-like solid (i.e., being formed from a closed path having a cross section that is substantially circular), or any other suitable shape, including without limitation, an ellipse (with a substantially elliptical cross section), a rectangle (with a substantially rectangular cross section), a triangle (with a substantially triangular cross section), a polygon (with a substantially polygonal cross section) or any combination of one or more of such geometric shapes. The shape of the void may also be selected from a variety of different geometric shapes, including without limitation, a circle, ellipse, rectangle, triangle, polygon, or some combination of one or more thereof, provided that the selected shape for the void will accommodate one or more fingers of a user. The voids in the first body, the second body, or both bodies, may be bounded by inward-facing rectilinear walls or inward-facing toroidal walls opposite from the circumferential grooves and fasteners. The first body, the second body, or both bodies, may also include one or more aeration holes extending from the void to the outward-facing surface in order to improve airflow and facilitate drying after rinsing the device in water during a flossing session.

In some embodiments, the first body, the second body, or both the first and second bodies may include a second fastener, disposed on a third section of the outward-facing surface, to provide an alternative location for securing the free end of the length of dental floss. Like the first fastener, the second fastener may comprise a depression in the outward-facing surface, a crown having a base wall, a niche in the base wall, and a pedestal that connects the base wall of the crown to the floor of the depression. It is understood, however, that the second fastener does not necessarily have the same shape and features as the first fastener. The dimensions of the base wall, the niche and the pedestal in the second fastener are also configured to provide a space between the floor of the depression and the base wall of the crown, the space being of sufficient size to receive and secure the section of the free end of the dental floss wound in a loop around the pedestal before passing into and through the niche in the base wall. Thus, the base wall, the pedestal, the space between the base wall and the pedestal, and the niche of the second fastener are also optimally arranged to provide a secure connection of the free end of the dental floss to the second fastener, and to provide a second bridge to support a portion of the one or more revolutions of dental floss carried by the circumferential groove, so that the one or more revolutions of dental floss carried by the circumferential groove may pass over the second fastener without being diverted or interfered with by the loop or loops of dental floss wrapped about the second pedestal. The crown in the second fastener may also include a pair of sidewalls configured to prevent the portion of the one or more revolutions of dental floss passing over the second bridge from slipping over the sides of the base wall in the second fastener.

In preferred embodiments, each cleat in the pair of cleats has a notch (or, alternatively, multiple notches located at opposite ends of the cleats) configured to permit a part of the length of dental floss to pass through the notch at an oblique angle relative to the direction or path of the revolutions of dental floss carried by the circumferential groove. When the part of the length of dental floss passing through the notch at the oblique angle is held under tension by the user, this notch acts as a stop to prevent the revolutions of dental floss carried in the circumferential groove from unwinding from the body and/or falling out of the circumferential groove while the device is being used for a flossing operation. The notch or notches may also be utilized to lock the free end of the dental floss to the body of the device while the device is not in use.

Additional embodiments, features and benefits of the invention will become apparent upon reading the detailed disclosure below. The invention may be embodied in the forms illustrated in the accompanying drawings, attention being called to the fact, however, that the drawings are illustrative only, and that changes may be made in the specific construction of the embodiments illustrated and described within the scope of the appended claims, without departing from the inventive aspects and scope of the invention.

BRIEF DESCRIPTION OF THE DRAWINGS

The present invention and various aspects, features and advantages thereof are explained in detail below with reference to exemplary, and therefore non-limiting, embodiments described and with the aid of the drawings, which constitute a part of this specification and include depictions of the exemplary embodiments. In these drawings.

DETAILED DESCRIPTION OF EXEMPLARY EMBODIMENTS

Figure 1:
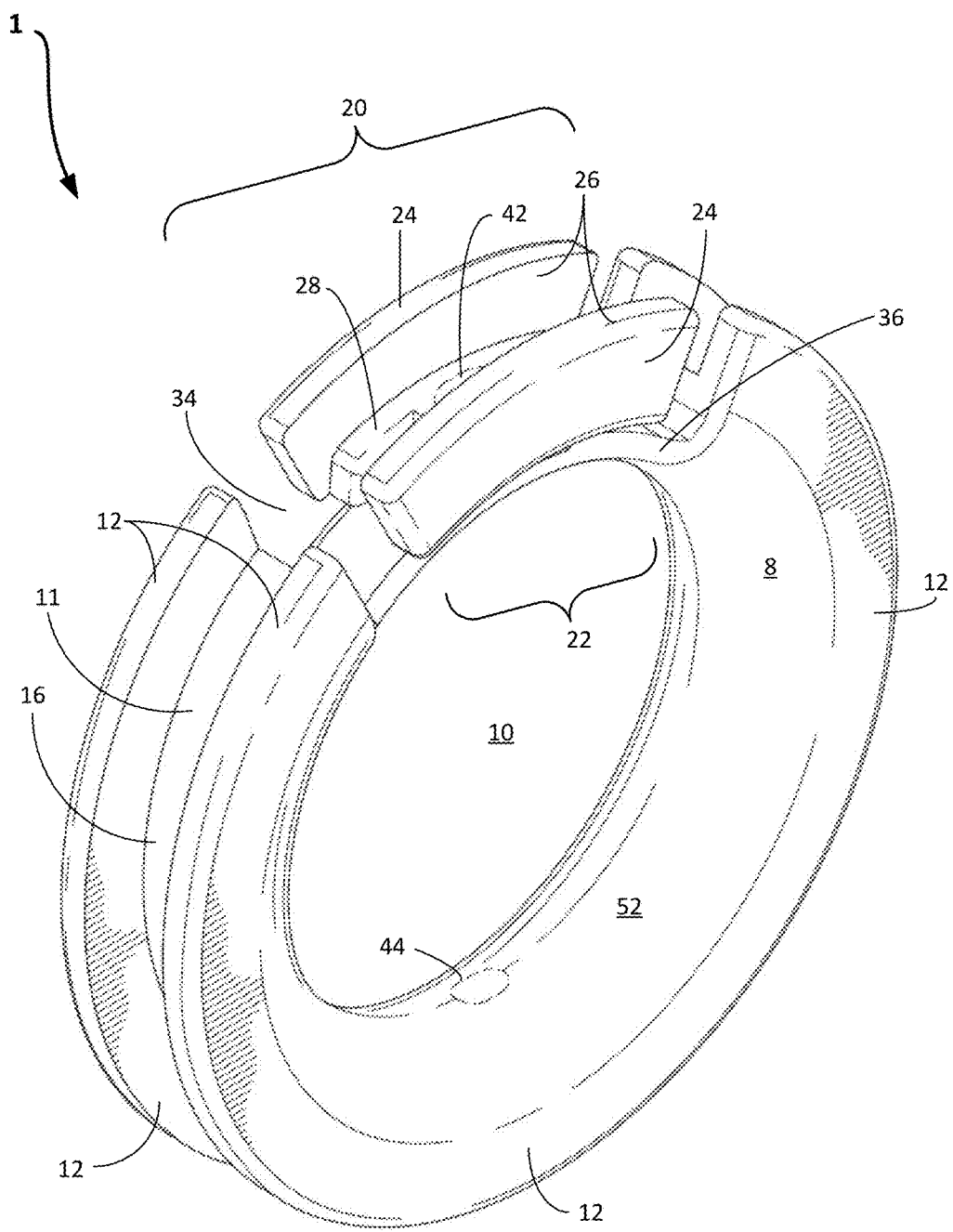
FIGS. 1 through 5 show, respectively, a perspective view, a front side elevational view, a right side elevational view, a top plan view and a bottom plan view of an exemplary dental flossing device according to a first embodiment of the present invention.

Exemplary devices according to certain embodiments of the invention will now be described in more detail with reference to the accompanying figures. Although the exemplary devices shown in the figures illustrate embodiments of the present invention in which the bodies have substantially ring-like shapes with substantially circular cross sections, it is anticipated and understood that other embodiments of the invention (not shown in the figures) may have a variety of other geometric shapes, including without limitation, ellipses, triangles, rectangles and other circular forms or polygons.

Turning now to the drawings, in which the same reference characters in multiple figures denote the same or similar elements throughout the several views, FIGS. 1 through 5 show, respectively, a perspective view, a front side elevational view, a right side elevational view, a top plan view and a bottom plan view of an exemplary dental flossing device 1 according to one embodiment of the present invention. It is understood that the rear side and left side elevational views of dental flossing device 1 (not shown in the figures) are mirror images of the front side and right side elevational views of dental flossing device 1, respectively.

Figure 2:
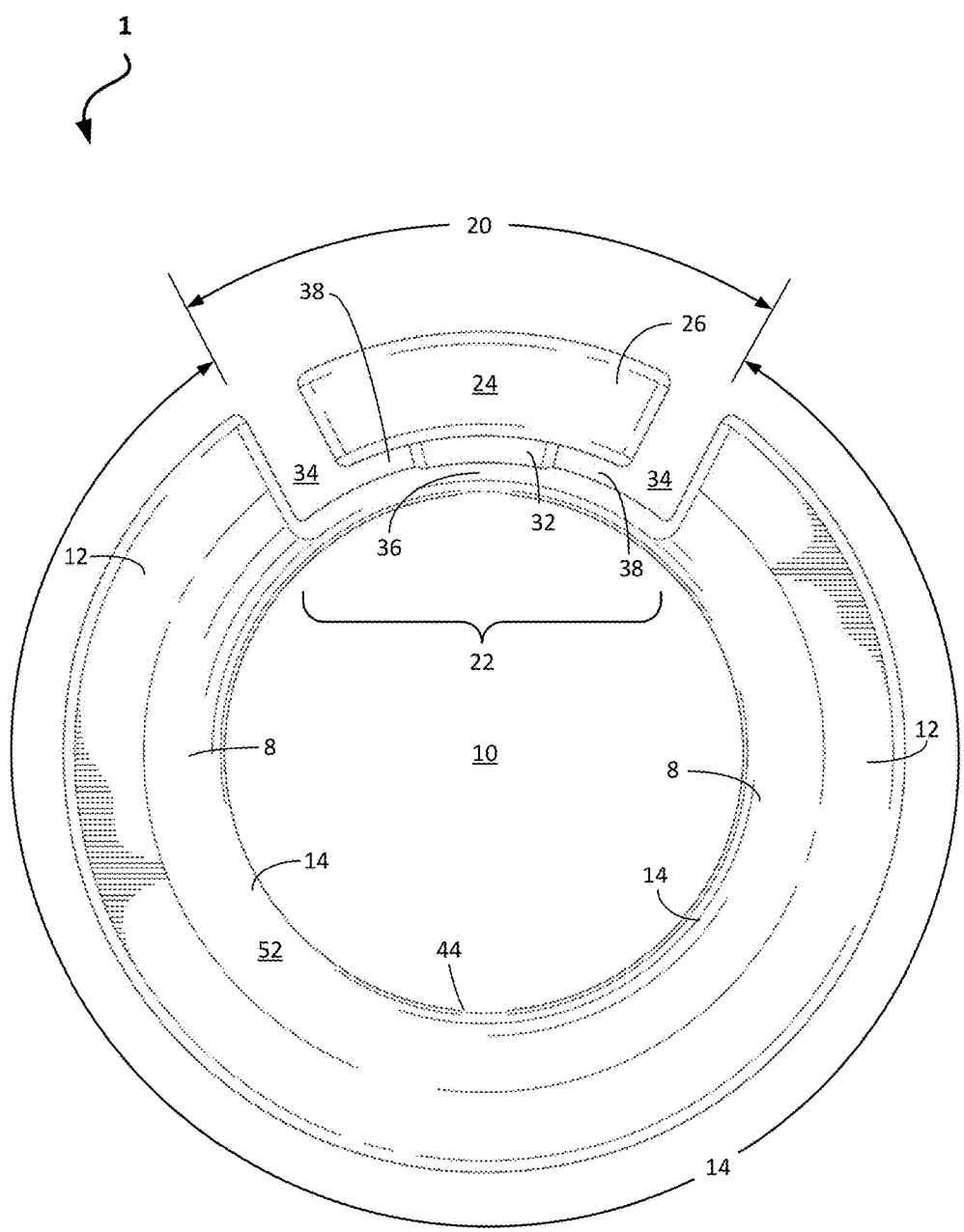
Figure 3:
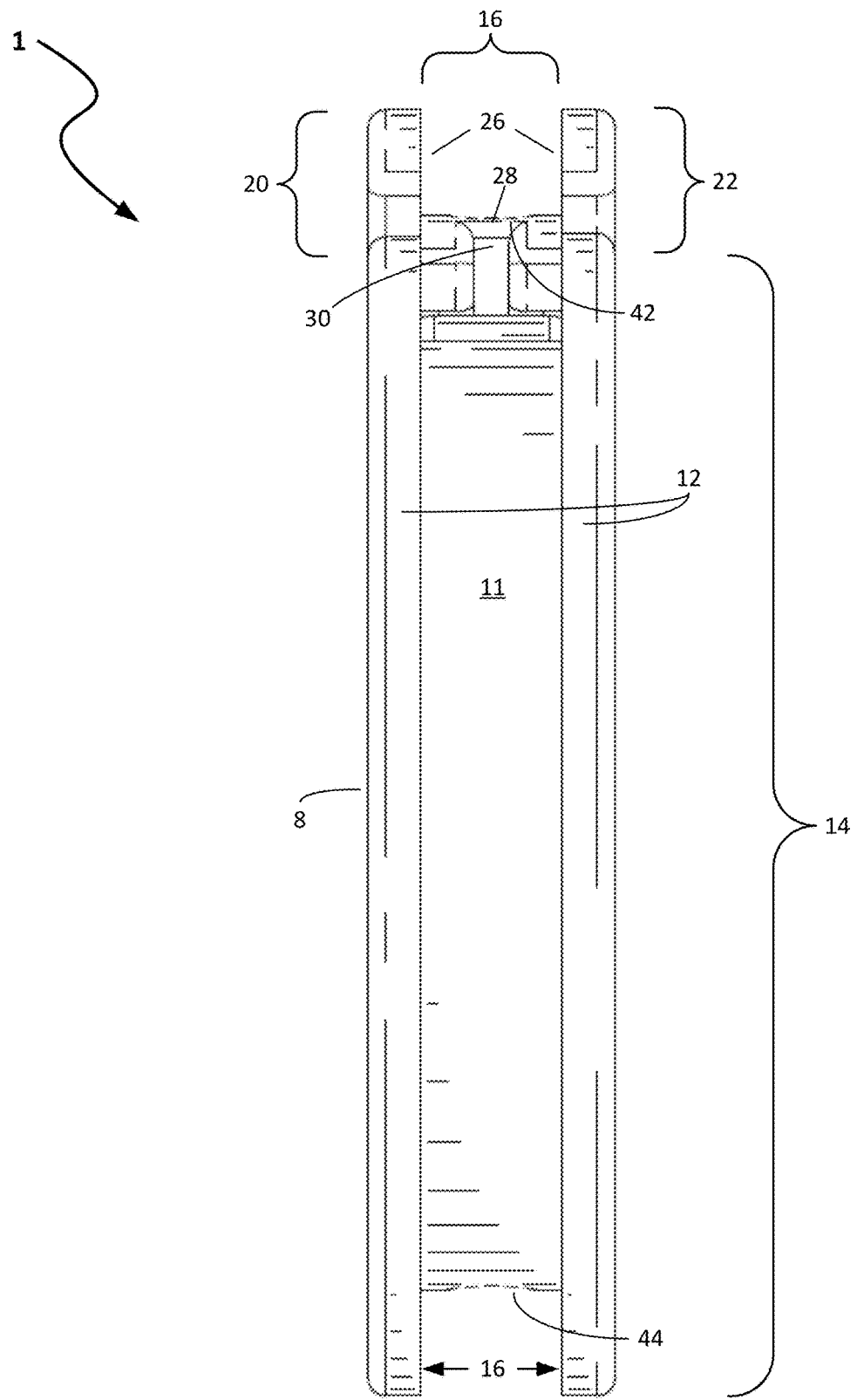
Figure 4:
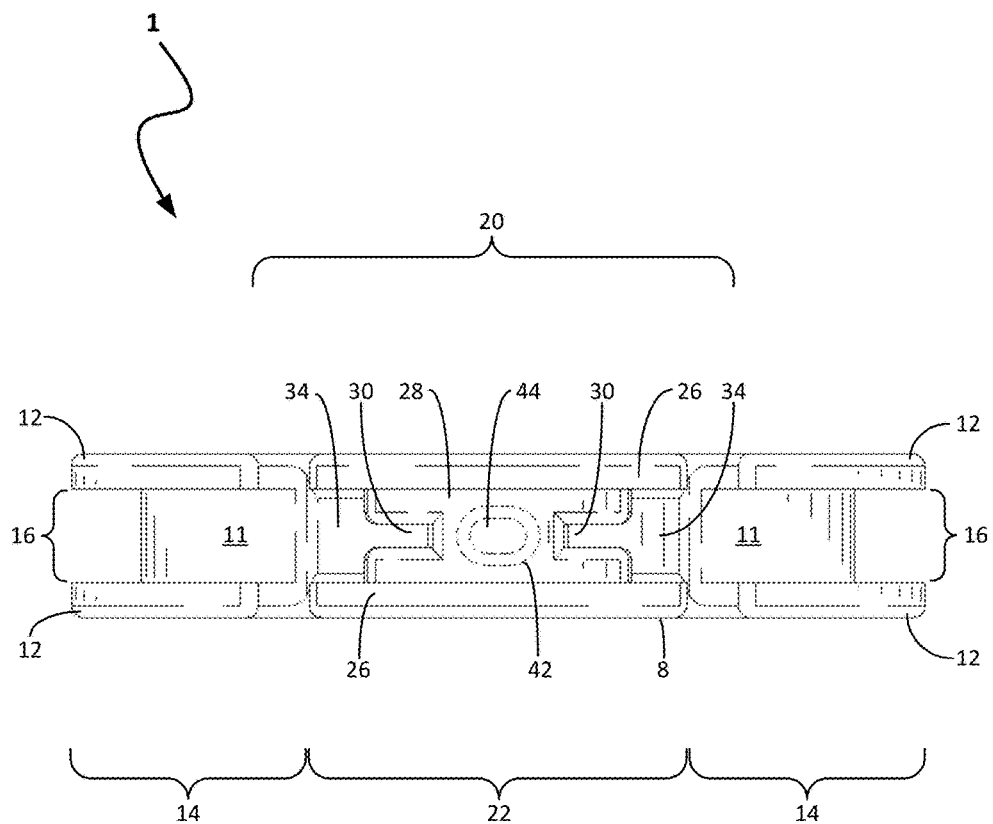
Figure 5:
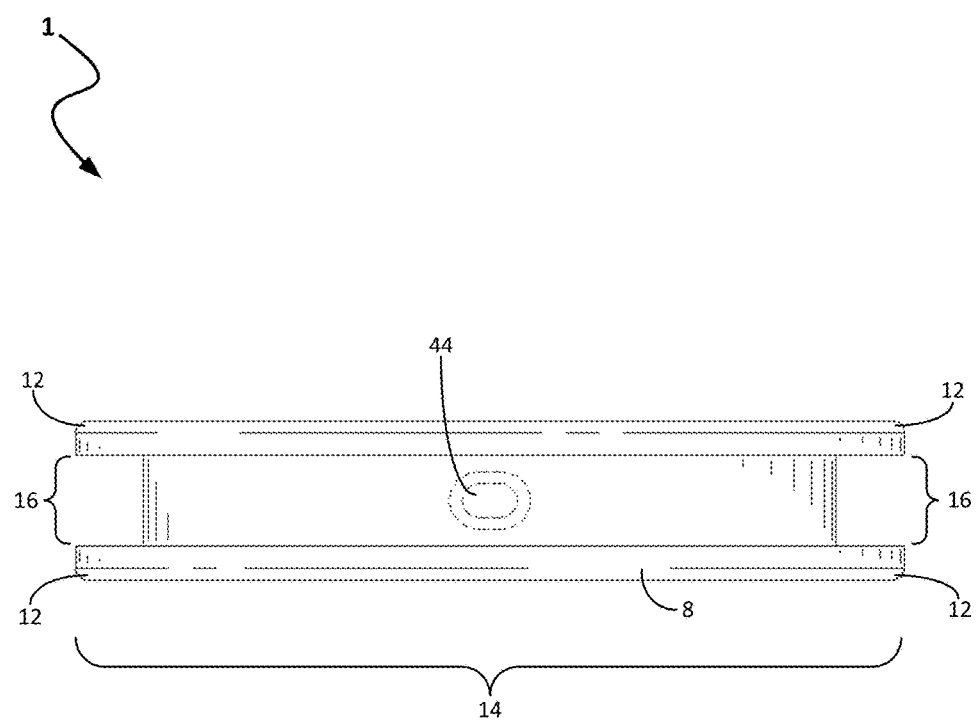
Figure 11:
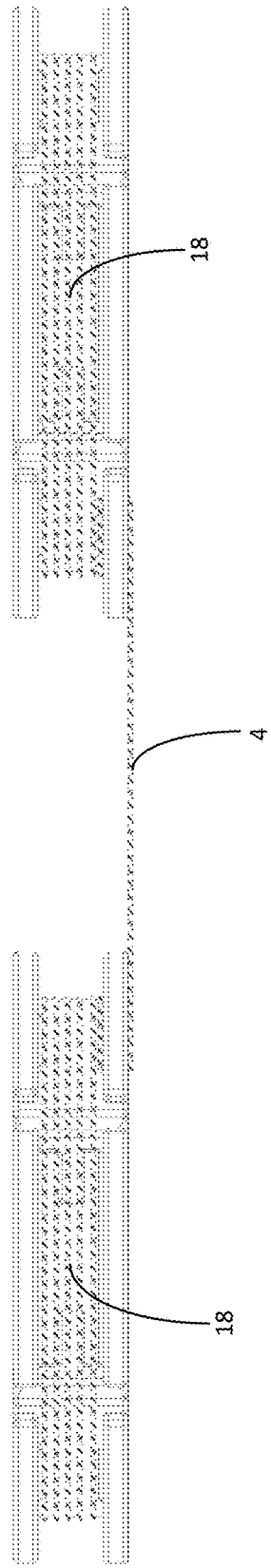

As shown in FIGS. 1-5, the dental flossing device 1 comprises a first body 8, in this case comprising a ring-like structure with a toroidal inner wall 52, circumscribing a void 10 adapted to receive one or more fingers (not shown in FIGS. 1-5) on the left or right hand of a user. The body 8 has an outward-facing surface 11, opposite from the void 10. As best shown in FIG. 2, the outward-facing surface 11 is divided into two segments 14 and 22. On the first segment 14 of the outward-facing surface 11, there is one pair of cleats 12 arranged to define between them a circumferential groove 16 adapted for receiving and carrying one or more revolutions 18 of the length of dental floss 4. The circumferential groove 16 is best shown in the right side elevational view of the dental flossing device 1 shown in FIG. 3. The length of dental floss 4 and the revolutions of dental floss 18 (which are shown best in FIGS. 8 and 11) are formed by wrapping the length of dental floss 4 around the body 8 so that the length of dental floss 4 turns into revolutions 18 that lie inside the circumferential groove 16 between the pair of cleats 12.

Referring again to FIG. 2, the second segment 22 of the outward-facing surface 11 includes a fastener 20 comprising a depression 34 in the outward-facing surface 11, a crown 24 with a base wall 28 and a niche 30 in the base wall 28. The fastener 20 also includes a pedestal 32 that connects the base wall 28 of the crown 24 to the floor 36 of the depression 34. The dimensions of the base wall 28, the niche 30 in the base wall 28, and the pedestal 32 are configured to provide a space 38 (or seat) located between the floor 36 of the depression 34 and the base wall 28 of the crown 24. The space 38 is of sufficient size to receive and secure a section of the free end 6 of the dental floss 4 as it is wound in a loop 40 about the pedestal 32, and then passed through and lodged within the niche 30 in the base wall 28. Passing the free end 6 of the length of dental floss 4 through the niche 30 aids in providing additional friction for securing the free end 6 of the dental floss 4 to the fastener 20. The length of dental floss 4 extending beyond the niche 30 is then wrapped into the circumferential groove 16 around the perimeter of the outward-facing surface 11 of the body 8. Thus, the base wall 28, the pedestal 32, the space 38 between the base wall 28, and the niche 30 are all arranged in a configuration that permits these elements to cooperate with one another so as to provide a more secure attachment of the free end 6 of the length of dental floss 4 to the body 8 while minimizing the amount of dental floss required for the secure attachment.

It is understood that the base wall 28 and the niche 30, as well as the depression 34, the pedestal 32 and the space 38 may vary in shape, size and orientation, as necessary, depending on the type and dimensions of the length of dental floss 4 used with the device 1. The niche 30 in the base wall 28 may be formed of any suitable shape and size, and may be oriented in any direction relative to the revolutions 18 supported by the bridge 42. For example, in some embodiments, the niche 30 comprises a cut, slot or slit that runs parallel to the direction of the revolutions 18 of dental floss supported by the bridge 42, while in other embodiments, the niche 30 may comprise a cut, slot or slit that runs perpendicular or on a diagonal relative to the revolutions 18 supported by the bridge 42. Embodiments of the present invention may also include one, two, three or more niches in the base wall 28. These niches, or at least one of them, may also be located in one or both of the sidewalls, or at the intersection of the base wall and one of the sidewalls. It is also understood that the pedestal 32 connecting the base wall 28 of the crown 26 to the floor 36 of the depression 34 can be of any suitable shape, including without limitation, a cylinder, triangular solid, rectangular solid, etc.

The base wall 28 of the crown 24 and the pedestal 32 connecting the base wall 28 to the floor 36 of the depression 34 are configured to provide a bridge 42 of sufficient height and appropriate orientation to support a portion of the one or more revolutions 18 of dental floss carried by the circumferential groove 16. The bridge 42 permits the portion of the dental floss revolutions 18 of dental floss passing over the fastener 20 to pass over the fastener 20 without coming into contact with the section of the free end 6 of the loop 40 of dental floss wrapped about the pedestal 32. In other words, the revolutions 18 of dental floss 4 carried by the circumferential groove 16 are held away from the floor 36 of the depression 34 by the bridge 42 so that the revolutions 18 carried by the circumferential groove 16 remain in a higher orbit (relative to the floor 36 of the depression 34) than the loops 40 wrapped about the pedestal 32. In this manner, the loops 40 of floss wrapped around the pedestal 32 do not divert, or otherwise interfere with, the revolutions 18 of the dental floss carried by the circumferential groove 16.

As best shown in FIGS. 1, 3, 4 and 5, embodiments of the present invention include a circumferential groove 16 interposed between a pair of cleats 12 that extend around the first section 14 of the outward-facing surface 11 of the first body 8 to provide a receptacle and structural support for the revolutions 18 of dental floss wound around the first body 8. The pair of cleats 12 prevent the revolutions 18 of dental floss from falling over the lateral edges of the outward-facing surface 11 of the body 8. The width and height of the circumferential groove 16 determine the volume of dental floss that can wound into the revolutions 18 on the body 8. Embodiments of the present invention may provide variations in the width and height of the pair of cleats 12 and the circumferential groove 16 so as to provide users with the ability to select from many of the different options in the type and amount of dental floss that can be wound stored on the device 2. For example, variations in width and height of the pair of cleats 12 and the circumferential groove 16 may permit users to store the appropriate amount of dental floss for multiple flossing sessions, multiple days, multiple weeks, a year, or anywhere in between.

In FIGS. 1-5, the pair of cleats 12 on the first segment 14 of the outward-facing surface 11 are parallel to each other, have roughly the same dimensions, and are positioned directly beside each other on the first section 14 of the outward-facing surface 11 of the first body 8. It is understood, however, that the cleats in the pair of cleats 12 may not be parallel to each other, may have different dimensions from each other, and/or may be arranged in a staggered fashion (not shown in the figures), relative to each other, along the first section 14 of the outward-facing surface 11 of the first body 8. As shown best in FIGS. 4 and 5, embodiments of the present invention may also include one or more aeration holes 44 in the body 8 of the device to provide airflow for the rings and facilitate drying when the device comes into contact with water and/or moisture.

Figure 6:
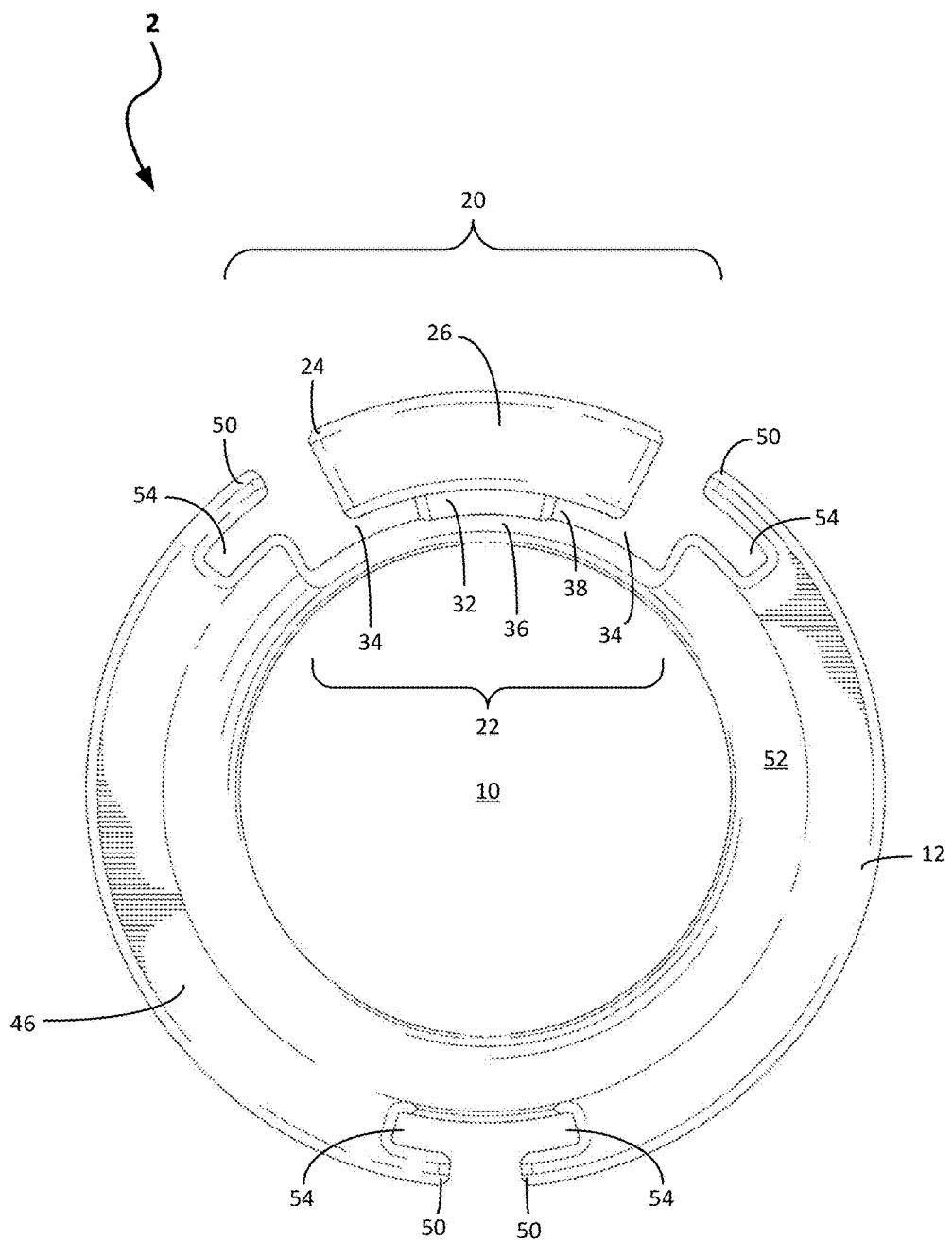
FIG. 6 shows a front side elevational view of another exemplary dental flossing device according to a second embodiment of the present invention, wherein the outward-facing surface has two pairs of cleats.
Figure 7:
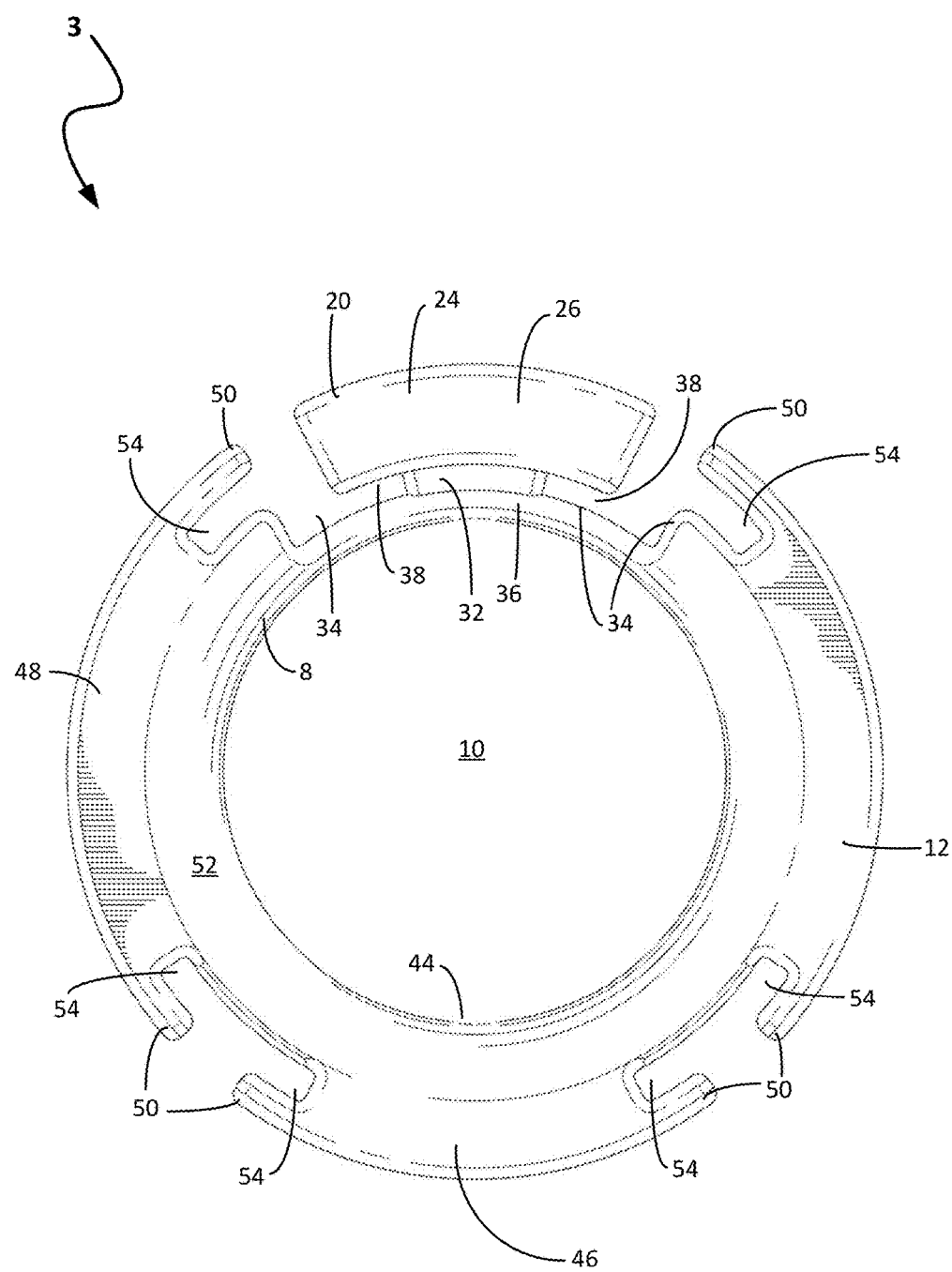
FIG. 7 shows a front side elevational view of yet another exemplary dental flossing device according to a third embodiment of the present invention, wherein the outward-facing surface has three pairs of cleats.
Figure 9:
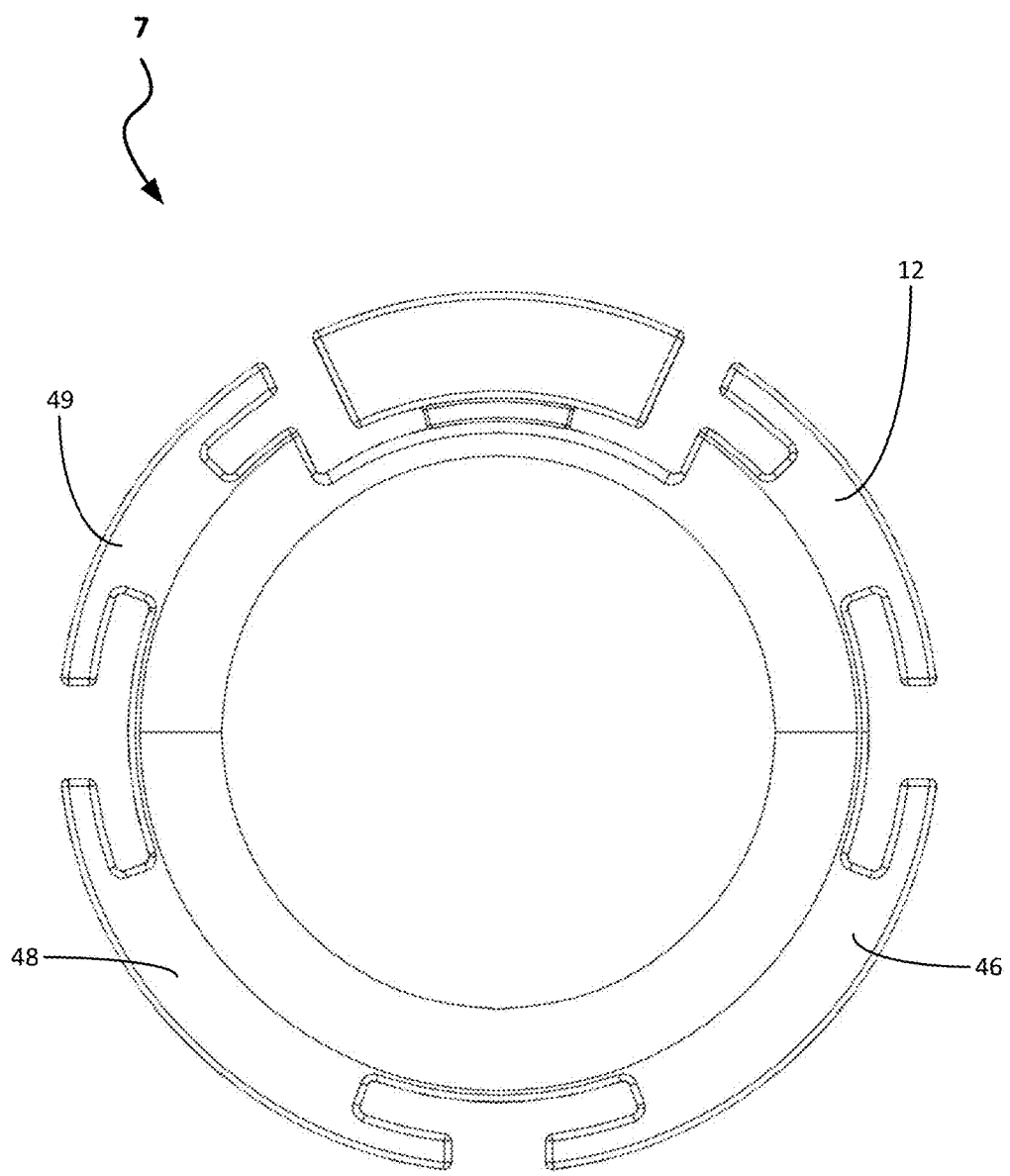
FIG. 9 shows a front side elevational view of still another exemplary dental flossing device according to a fourth embodiment of the present invention, wherein the outward-facing surface has four pairs of cleats.
Figure 10:
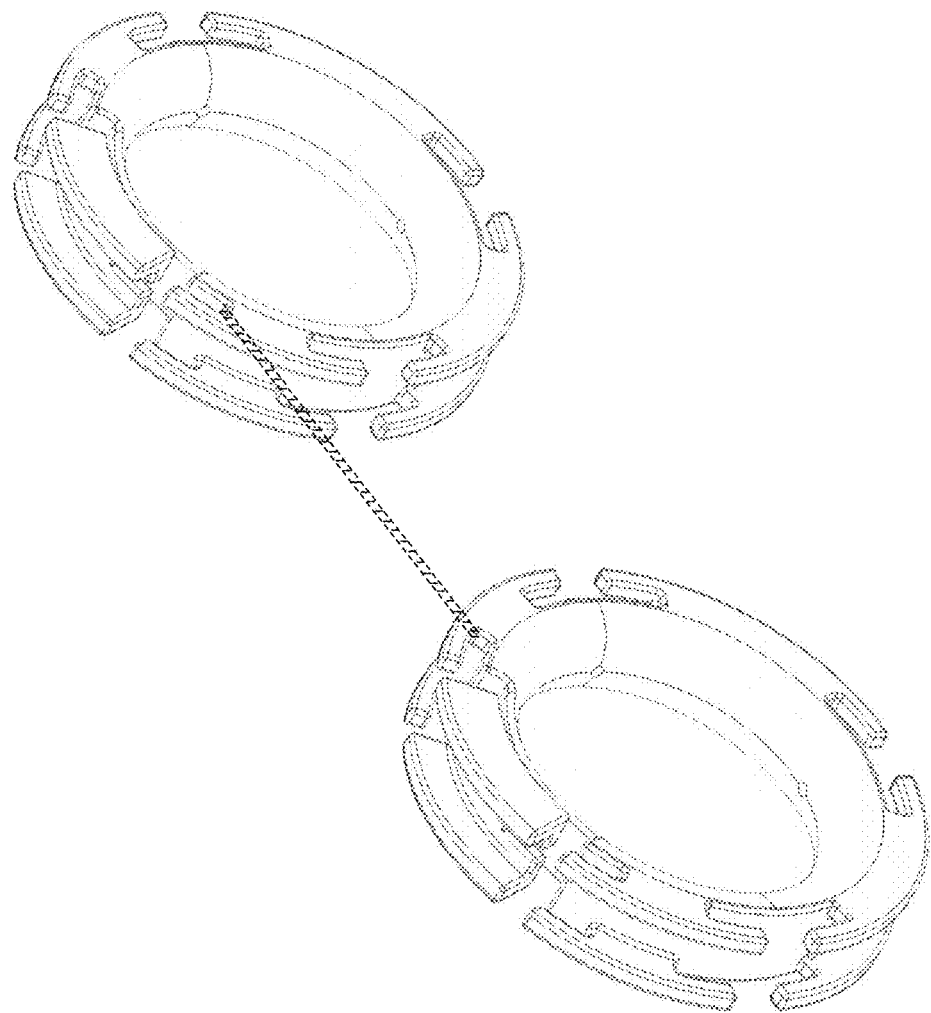
FIGS. 10 and 11 show, respectively, a perspective view and a top plan view of the exemplary dental flossing device depicted in FIG. 9 as it might be used in tandem with a second identical unit and loaded with dental floss in accordance with another implementation of the present invention.

In alternative embodiments of the present invention, multiple pairs of cleats may be positioned around the first section 14 of the outward-facing surface 11 of the first body 8. To illustrate such an embodiment, FIG. 6 shows a front side elevational view of another exemplary dental flossing device 2 configured according to a second embodiment of the present invention, wherein the first section 14 of the outward-facing surface 11 has two pairs of cleats 12, 46, defining the circumferential groove 16. FIG. 7 shows yet another exemplary dental flossing device 3, in which the outward-facing surface 11 of the body 8 has three pairs of cleats 12, 46 and 48 in the first section 14 of the outward facing surface 11. Similarly, FIG. 9 shows still another exemplary dental flossing device 7, in which the outward-facing surface 11 of the body 8 has four pairs of cleats 12, 46, 48 and 49 on the first section 14 of the outward facing surface 11. Notably, the pairs of cleats in the first section 14 may not all be of the same length. For example, as shown in FIG. 9, the pairs of cleats 46, 48 and significantly longer than the pairs of cleats 12, 49.

Unlike the exemplary dental flossing device 1 shown in FIGS. 1-5, the pairs of cleats 12, 46, 48 and 49 on the exemplary dental flossing devices 2, 3, 5 and 7 shown in FIGS. 6 through 11 contain multiple sets of prongs 50 and notches 54 located at opposite ends of the pairs of cleats 12, 46, 48 and 49, which are configured to permit a part of the length of dental floss 4 to pass through one of the notches 54 at an oblique angle relative to the path and direction of the revolutions 18 of dental floss carried by the circumferential groove 16. When the part of the length of dental floss 4 that passes through one of these notches 54 at the oblique angle is held under tension by the user, this notch 54 will act as a stop to prevent the revolutions 18 of dental floss carried in the circumferential groove 16 from unwinding from the body 8 and falling out of the circumferential groove 16 while the device 2, 3, 5 and 7 are being used for a flossing operation or being stored for later use.

Figure 8:
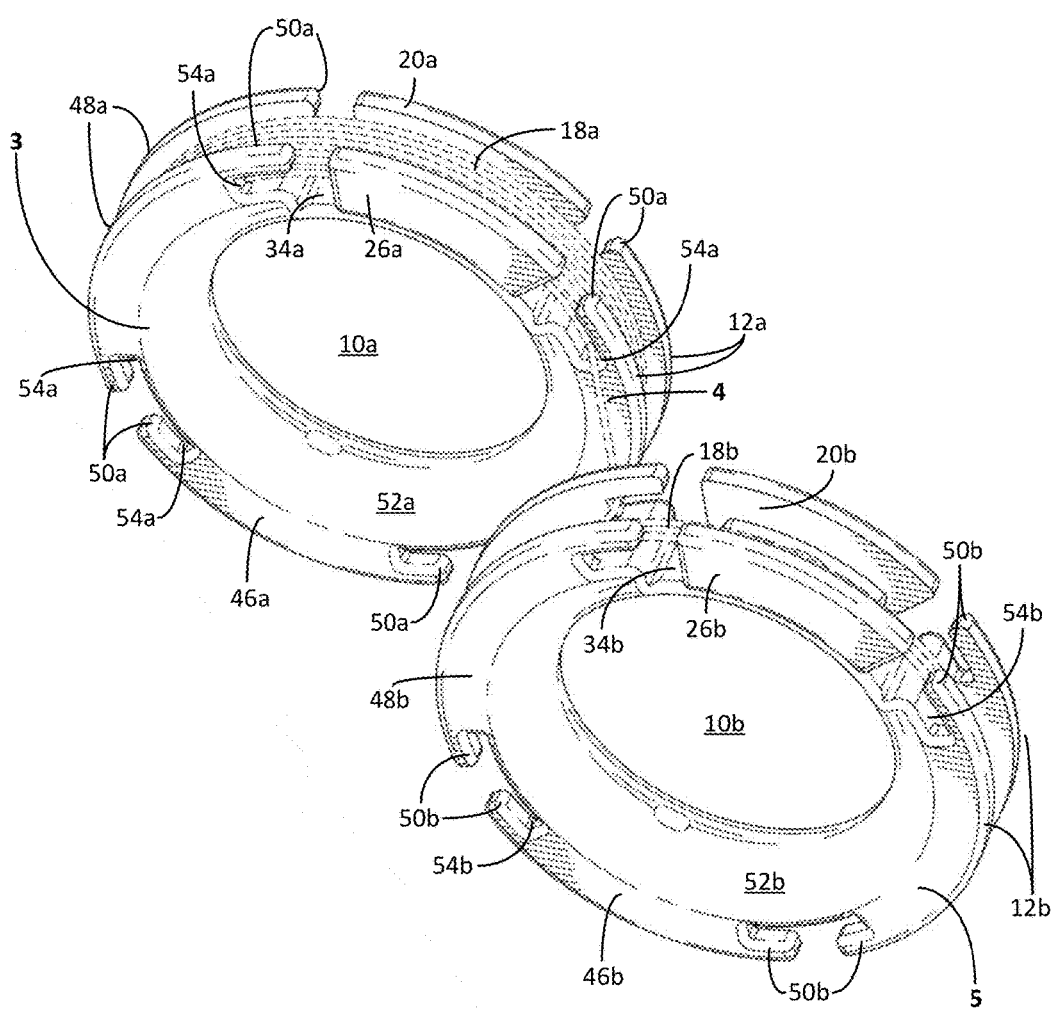
FIG. 8 shows a perspective view of the exemplary dental flossing device depicted in FIG. 7 as it might be used in tandem with a second identical unit and loaded with dental floss in accordance with one implementation of the present invention.

FIG. 8 shows a perspective view of the exemplary dental flossing device 3 depicted in FIG. 7 as it might be used in tandem with a companion dental flossing device 5 having the same shape and features of dental flossing device 3, and loaded with a length of dental floss 4. As shown in FIG. 8, companion devices 3 and 5, are connected by a length of dental floss 4 extended between them so that device 5 may be used as a take-up ring while device 3 may be used as a dispensing ring. However, because devices 3 and 5 contain exactly the same shape and features, they are interchangeable in performing in either the role of the take-up ring or the dispensing ring, based on user preference. For example, both devices 3 and 5 have circumferential grooves defined by the pairs of cleats 12a, 12b, 46a, 46b, 48a and 48b for carrying the revolutions 18a, 18b of dental floss wrapped about the bodies of devices 3 and 5 in accordance with one implementation of the present invention. Both devices 3 and 5 also include fasteners 20a, 20b, depressions 34a, 34b, sidewalls 26a. 26b, multiple sets of cleat prongs 50a, 50b and multiple notches 54a, 54b. Both devices 3 and 5 also have inward-facing toroidal walls 52a and 52b circumscribing the voids 10a and 10b.

In addition to the dental flossing devices 3 and 5 of FIG. 8 having all of the same dimensions and design features (making the devices identical), embodiments and implementations of the invention may also call for making the devices 3 and 5 symmetrical. Devices that are both identical and symmetrical in design are preferred because they eliminate considerations and decisions by the user regarding the orientation, direction, and their own left or right-handedness. Moreover, it permits both devices 3 and 5 to serve as the dispensing device or the take-up device when using the devices 3 and 5 together. Other embodiments, however, may use a variety of independent shapes and diameters and design configurations so that the companion devices 3 and 5 are not identical or symmetrical. In these embodiments (not shown in the figures), it may be necessary or desirable to make the companion devices distinct from each other in order to optimize one or both of the companion devices for performing a specific function. As just fare example, one of the companion devices may be specially formed and optimized solely to store and dispense fresh and unused dental floss, while the other companion device may be specially formed and optimized solely to receive and temporarily store used and soiled dental floss.

As shown in FIG. 8, the length of dental floss 4 wrapped around device 3 to form revolutions 18a also passes underneath one of the prongs 50a and through one of the notches 54a at an oblique angle to the direction of the revolutions 18a in the circumferential groove on dental flossing device 3. The notches 54a, 54b act as stops and the angle and tension of the length 4 of dental floss passing through the notches 54a, 54b and extended between the devices 3 and 5 prevents the revolutions 18a and 18b on devices 3 and 5, respectively, from unraveling and/or slipping off the devices 3 and 5 while the devices are manipulated in different planes and at various angles to each other. The voids 10a and 10b in devices 3 and 5 allow users to grip and hold the devices 3 and 5 with a single finger on each hand, to apply tension to the length of dental floss 4 extended between the device 3 and 5, and to rotate the devices 3 and 5 while manipulating the extended dental floss 4 using the thumbs and forefingers (see FIG. 21 discussed below). Griping devices 3 and 5 and applying the tension in this manner also permits the user to easily guide the extended length of dental floss 4 to locations in the mouth and between the teeth as required for proper flossing. Alternatively, and based on user preference, the palms and fingers of each hand can be used to grip the devices 3 and 5 without the user inserting any of his or her fingers through the voids 10a, 10b.

Figure 12:
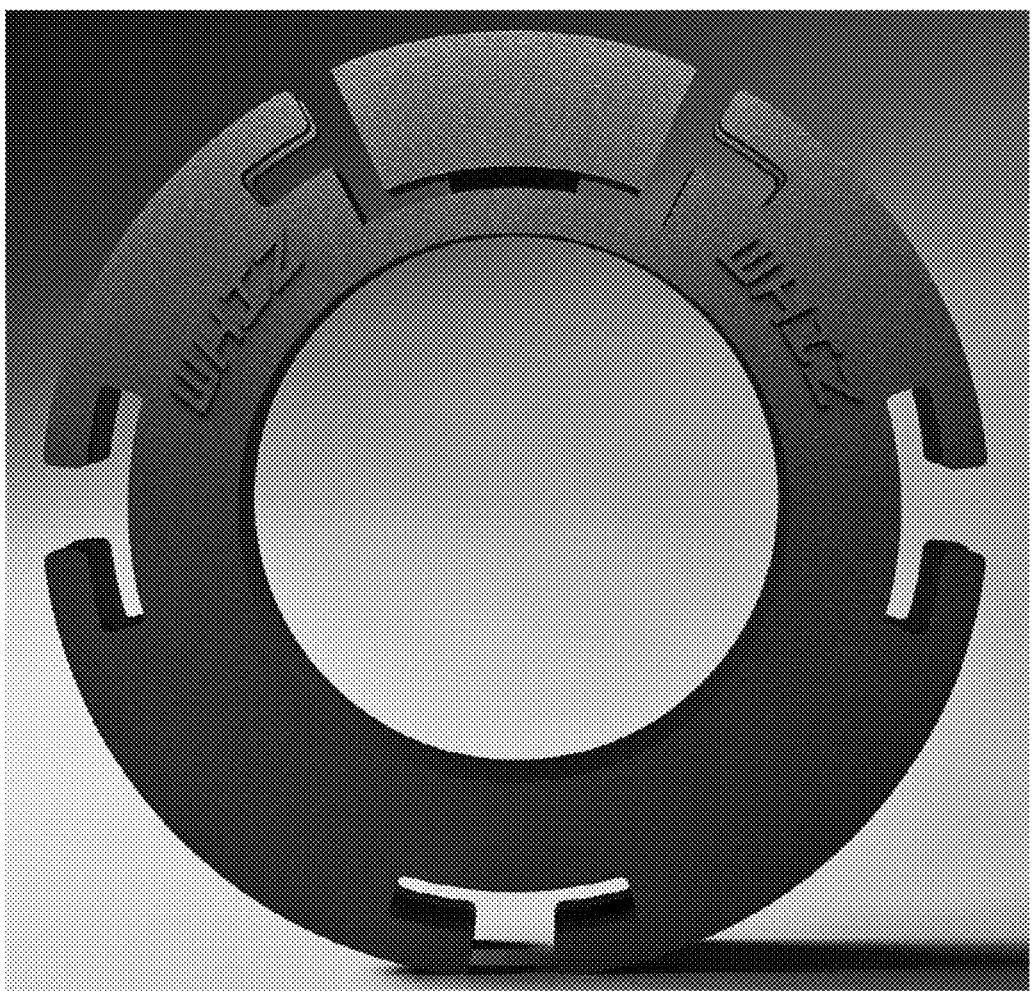
FIGS. 12 and 13 show, respectively, a front elevational view and a perspective view of still another exemplary dental flossing device according to a fifth embodiment of the present invention, wherein the walls of the dental flossing device are rectilinear.
Figure 13:
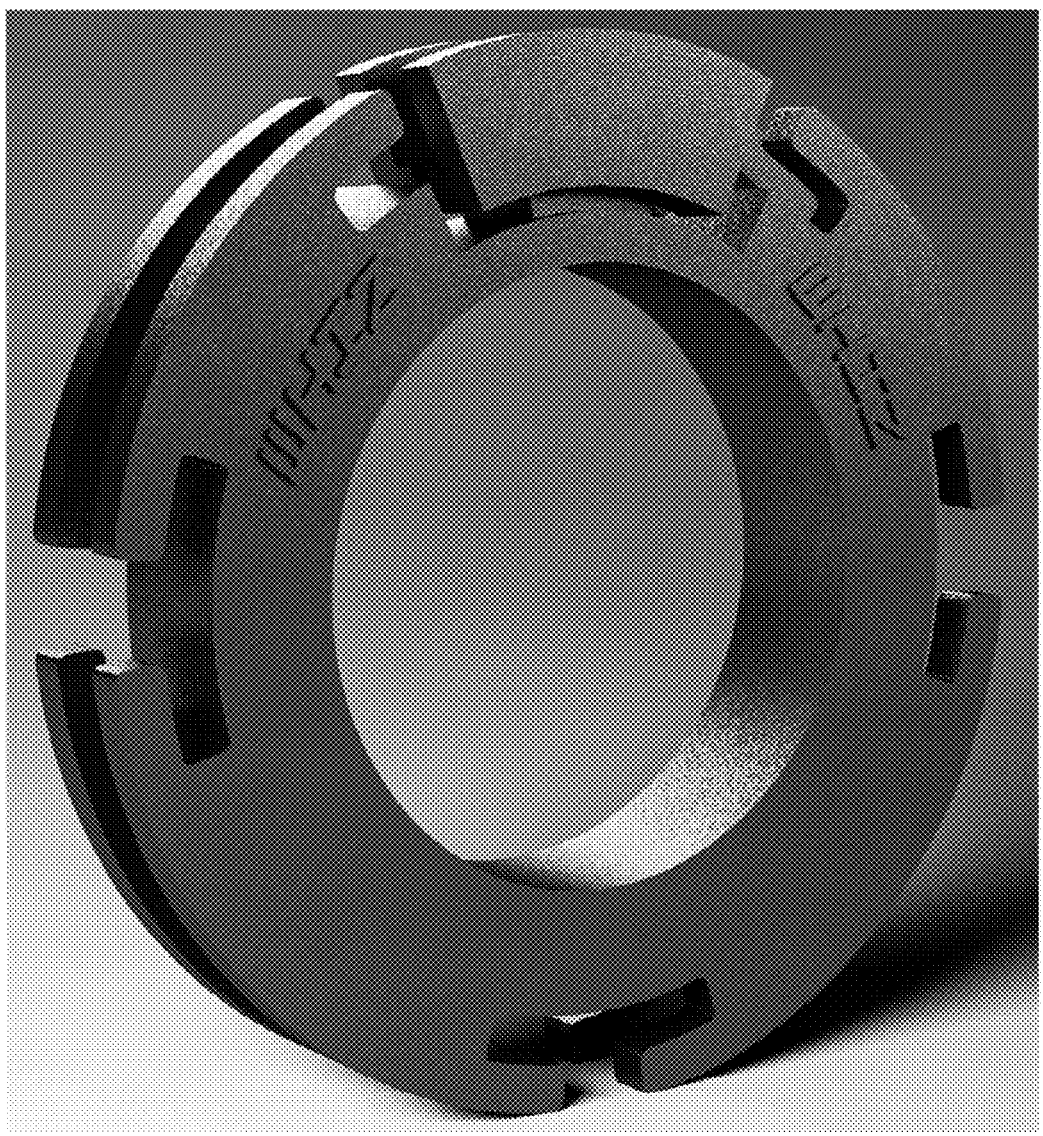
Figure 14:
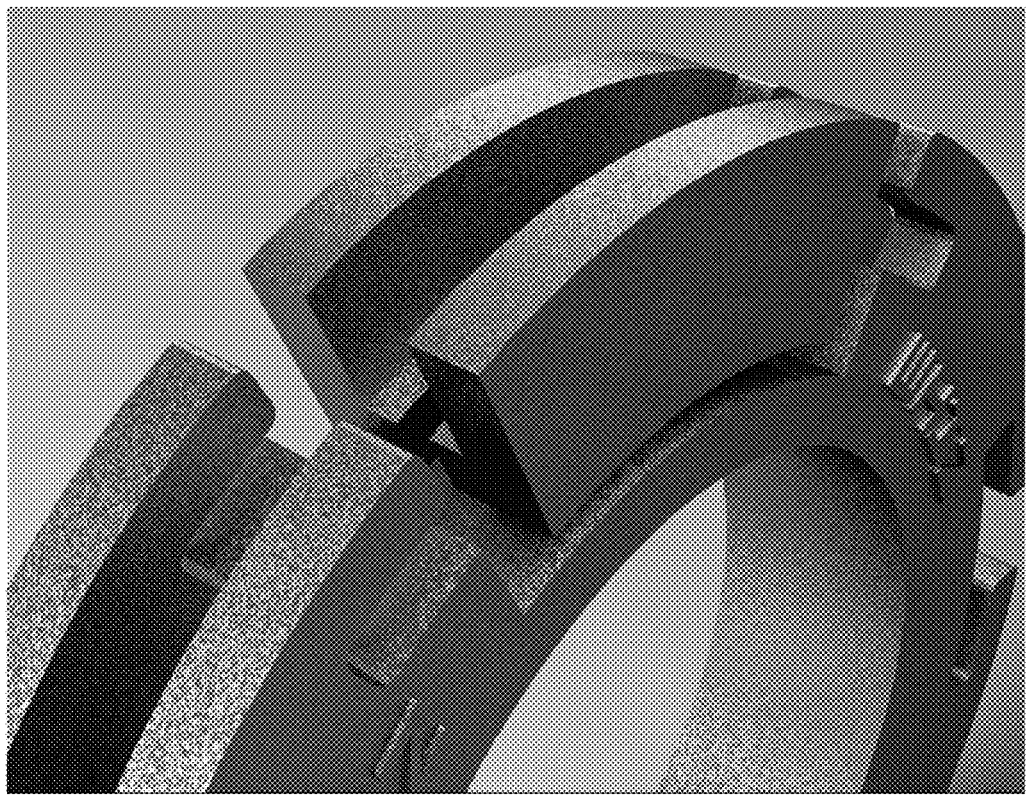
FIG. 14 shows a close up perspective view of the fastener on the exemplary dental flossing device depicted in FIGS. 12 and 13.

Continuing with the description of the devices 3 and 5 shown in FIG. 8, the diameters of the voids 10a and 10b of the ring-shaped dental flossing devices 3 and 5 are appropriately sized to fit comfortably on one or more fingers of a user and permit the user to rotate the devices 3 and 5 freely by using the thumbs and/or forefingers of each hand. Different sized diameters may be used to accommodate larger hands and fingers (e.g., for men and/or larger adults) or smaller hands and fingers (e.g., for women and/or children). The devices 3 and 5 may be rotated synchronously (or asynchronously) so that the length of dental floss 4 extended between the devices 3, 5 will move in the direction of the device 5, thereby causing the device 5 to take up used dental floss and increasing the number of revolutions 18b of dental floss wrapped about device 5. The inward-facing toroidal walls 52a, 52b minimize the contact between the user's fingers and the devices 3 and 5 so that the devices 3 and 5 rotate more freely. The inward-facing toroidal walls 52a, 52b also provide users greater comfort around the fingers by eliminating potentially sharp edges associated with an embodiment of the present invention having a rectilinear inward-facing wall. An example of an embodiment of the present invention having rectilinear walls and surfaces is shown in FIGS. 12, 13 and 14. Preferred embodiments of the present invention may also include textured surfaces (not shown) designed to make the devices easier to hold while flossing or loading fresh dental floss.

Figure 15:
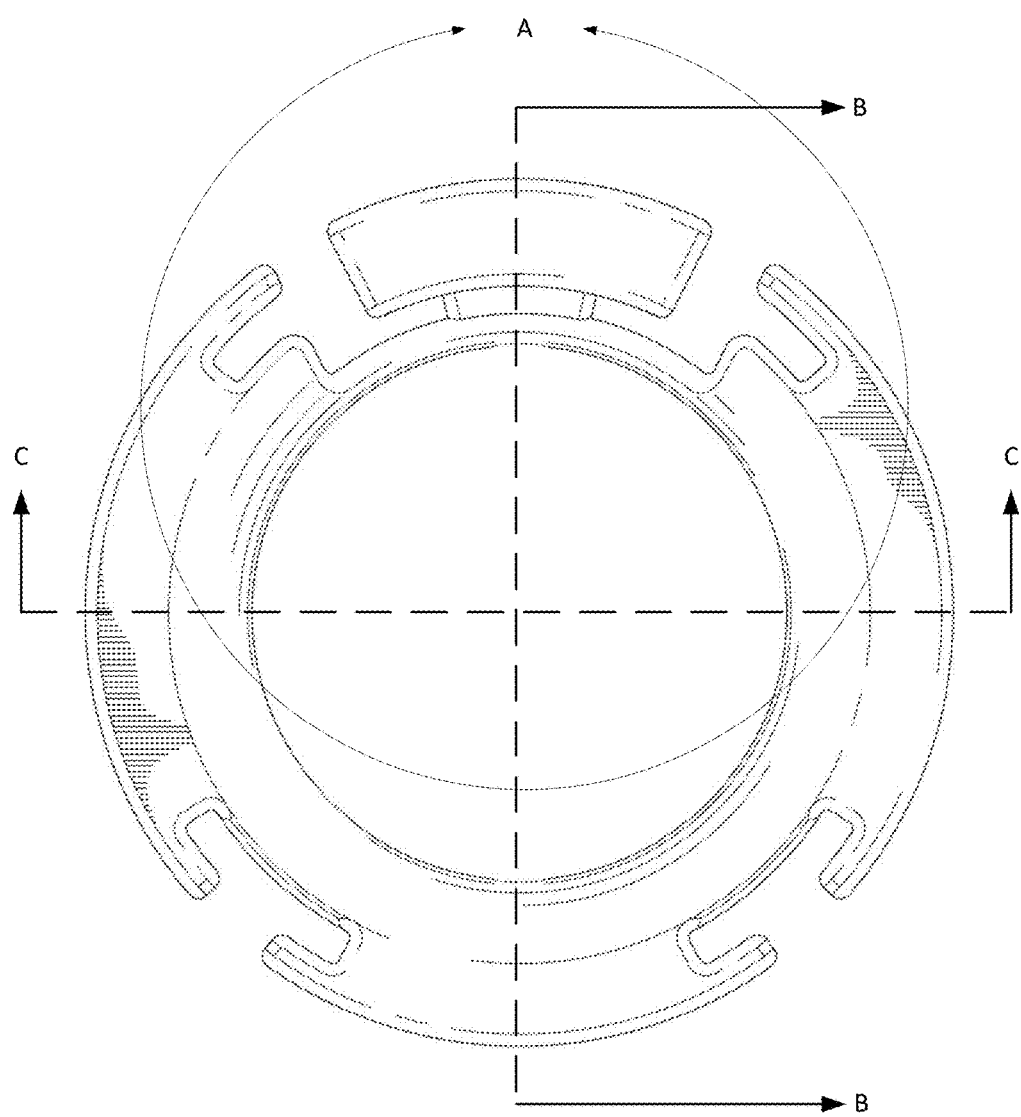
FIG. 15 shows a front side elevational view of the exemplary dental flossing device depicted in FIGS. 7 and 8 according to the third embodiment of the present invention, wherein the outward-facing surface has three pairs of cleats, except that FIG. 15 is simplified and annotated to illustrate the area of focus for the close-up view shown in FIG. 16 and to illustrate the cuts and directions of view for the cross sectional views shown in FIGS. 17, 18 and 19.
Figure 16:
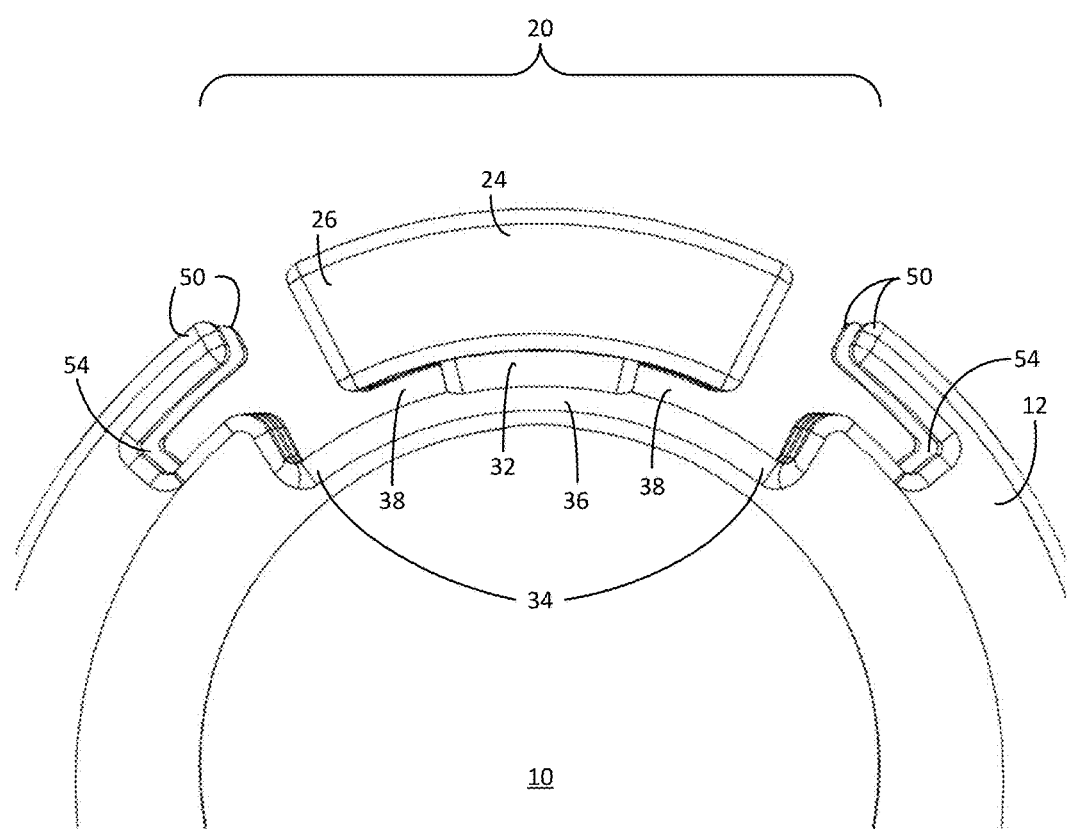
FIG. 16 shows a close-up view of the area in arc A of FIG. 15, which surrounds the fastener portion of the exemplary dental flossing device depicted in FIGS. 7 and 8 in accordance to the third embodiment of the present invention.
Figure 17:
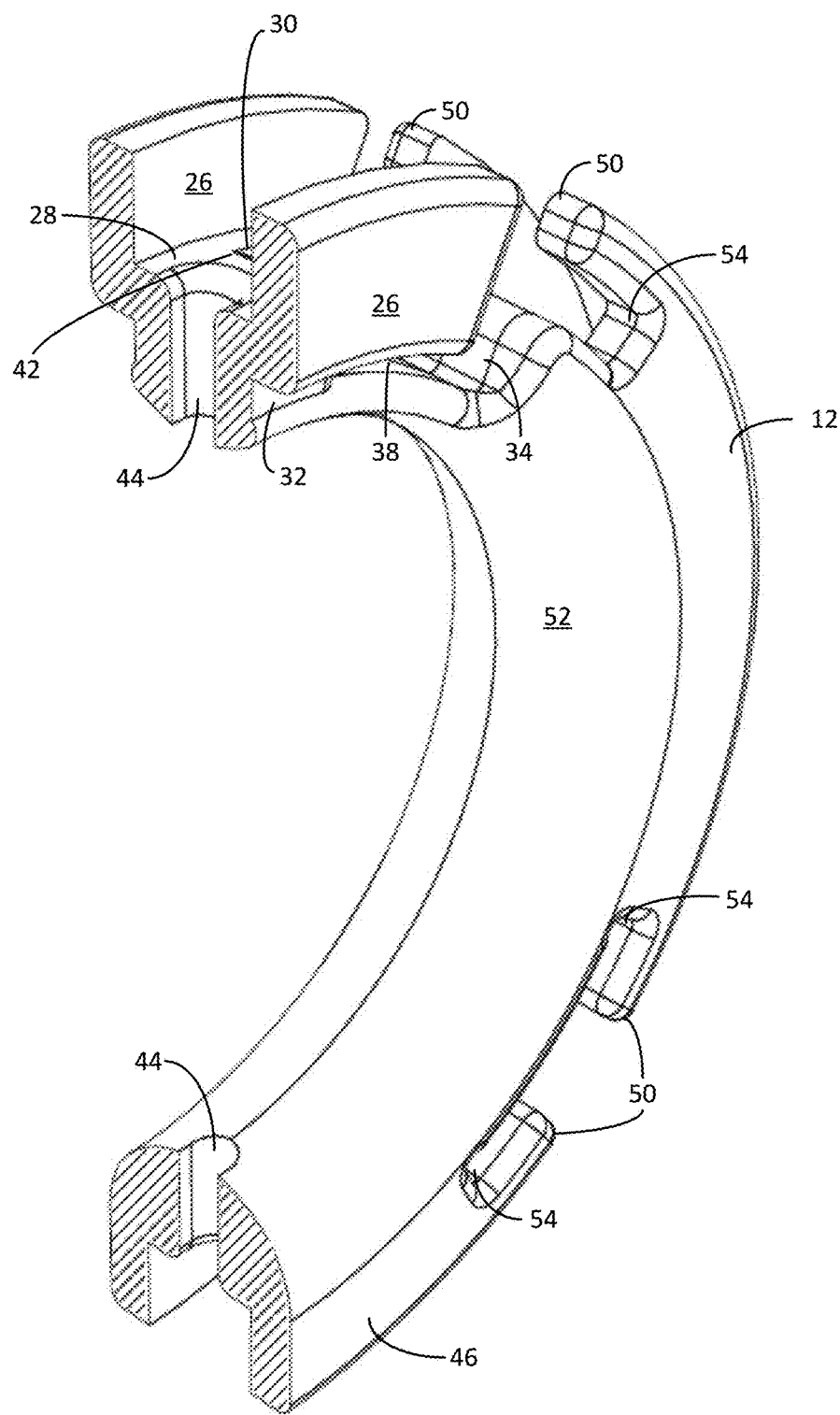
FIG. 17 shows a perspective view of the cross section of the exemplary dental flossing device depicted in FIGS. 7 and 8 according to the third embodiment of the present invention, wherein the cross section is taken along the line B-B of FIG. 15.
Figure 18:
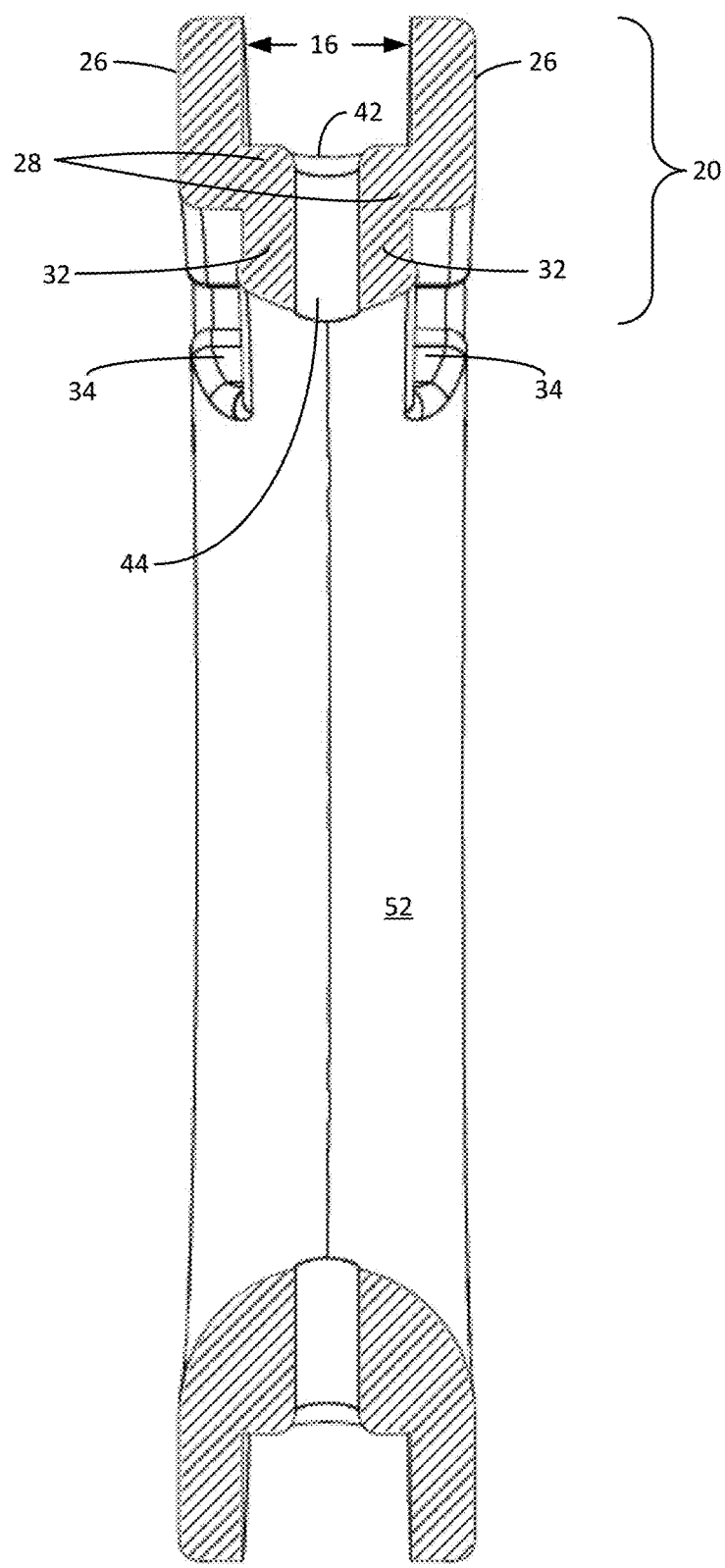
FIG. 18 shows an orthogonal view of the cross section of the exemplary dental flossing device depicted in 17.
Figure 19:
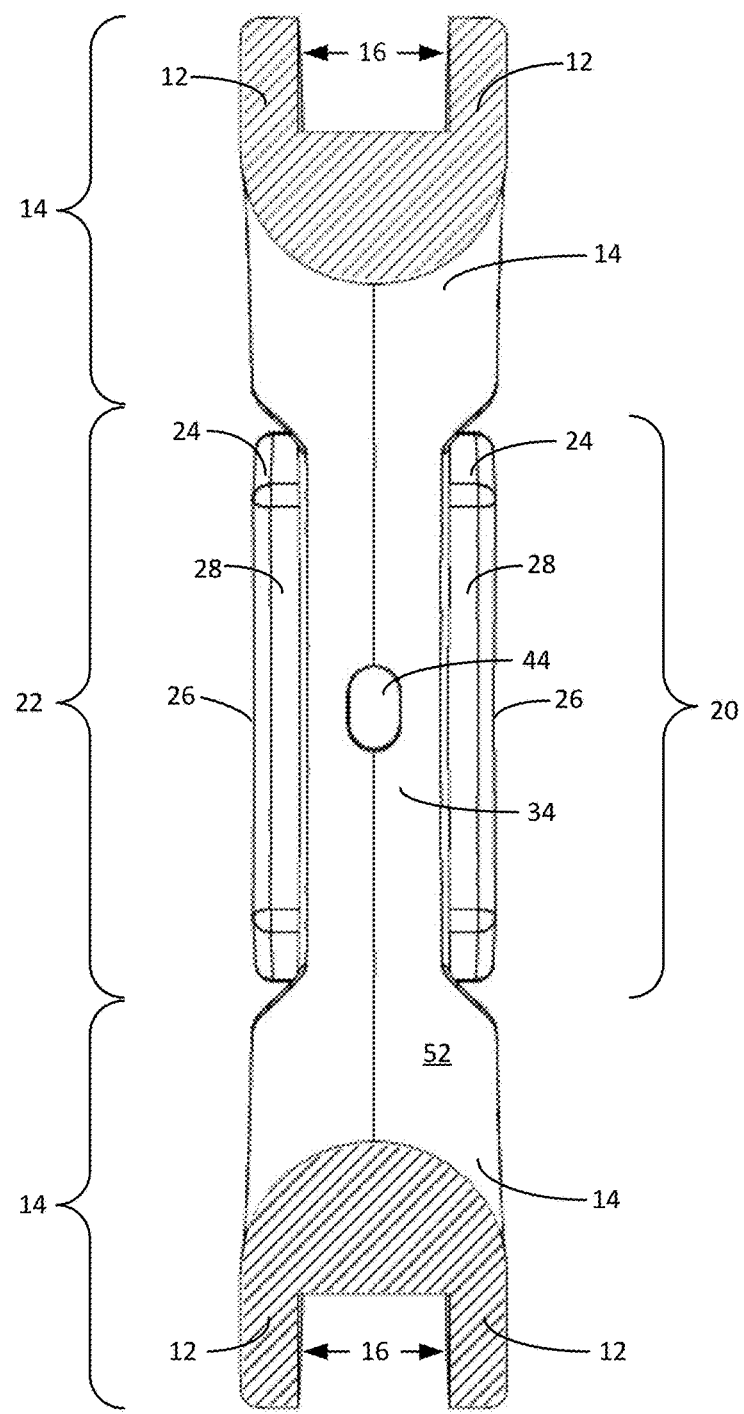
FIG. 19 shows an orthogonal view of the cross section of the exemplary dental flossing device depicted in FIGS. 7 and 8 according to the third embodiment of the present invention, wherein the cross section is taken along the line C-C of FIG. 15.

FIG. 15 shows a front side elevational view of the exemplary dental flossing device 3 depicted in FIGS. 7 and 8 according to the third embodiment of the present invention, wherein the outward-facing surface has three pairs of cleats, except that FIG. 15 is simplified and annotated to illustrate the area of focus for the close-up view shown in FIG. 16 and to illustrate the cuts and directions of view for the cross sectional views shown in FIGS. 17, 18 and 19. FIG. 16 shows a close-up view of the fastener for the exemplary dental flossing device depicted in FIGS. 7 and 8 according to the third embodiment of the present invention. FIG. 17 shows a perspective view of the cross section of the exemplary dental flossing device depicted in FIGS. 7 and 8 according to the third embodiment of the present invention, wherein the cross section is taken along the line B-B of FIG. 15. FIG. 18 shows an orthogonal view of the cross section of the exemplary dental flossing device depicted in 17. FIG. 19 shows an orthogonal view of the cross section of the exemplary dental flossing device depicted in FIGS. 7 and 8 according to the third embodiment of the present invention, wherein the cross section is taken along the line C-C of FIG. 15.

As shown best in FIGS. 16, 18 and 19, the dental flossing device of the present invention includes a fastener 20 for attaching the free end of a length of dental floss. The fastener 20 comprises a depression 34, a crown 24 and a pedestal 32 that attaches the crown 24 to the floor 36 of the depression 34. The depth of the depression 34, the width and height of the pedestal 32, and the width and depth of the crown 24 are configured to provide a space 38 between the floor 36 of the depression 34 and the base wall 28 of the crown 24 for receiving one or more loops 40 of dental floss wrapped around the pedestal 32.

As shown best in FIGS. 16, 18 and 19, the length and the width of the pedestal-facing surface of the base wall 28 of the crown 24 may be larger than the length and width of the pedestal 32. The larger dimensions of the bottom surface of the base wall 28 (as compared to the dimensions of the pedestal 32) provide a substantial physical barrier that aids in securing the loops 40 in place around the pedestal 32 and maintaining physical separation between the loops 40 of dental floss wrapped around the pedestal 32 and the revolutions 18 of extra dental floss wrapped around the circumferential groove 16. In preferred embodiments, the crown 24 also has a pair of side walls 26, connected to the base wall 28 of the crown 24. These sidewalls 26 are arranged to extend outward from the base wall 28 to provide lateral support for the revolutions 18 of dental floss carried by the circumferential groove 16 and to prevent the revolutions 18 of dental floss supported by the bridge 42 from slipping over the lateral sides of the base wall 28. Thus, the sidewalls 26 of the crown 24 aid in keeping the sections of the revolutions 18 of extra dental floss resting on top of the bridge 42 substantially in line with the sections of the revolutions 18 of the dental floss carried by the circumferential groove 16.

FIGS. 20A-20G show a series of diagrams illustrating by way of example how to attach a length of dental floss 4 to a dental flossing device 3 according to one embodiment of the present invention. For clarity and ease of comprehension. The device 3 is shown without either one of the optional sidewalls 26 shown in the rest of the figures. In other words, the sidewalls 26 connected to the base wall 28 in FIGS. 1 through 19 and 21 have been deleted from FIGS. 20A through 20G so as not obscure the base wall 28 and the niche 30 in the base wall 28, and thereby better illustrate the mechanism and the procedure for attaching the length of dental floss 4 to the device 3.

Figure 20A:
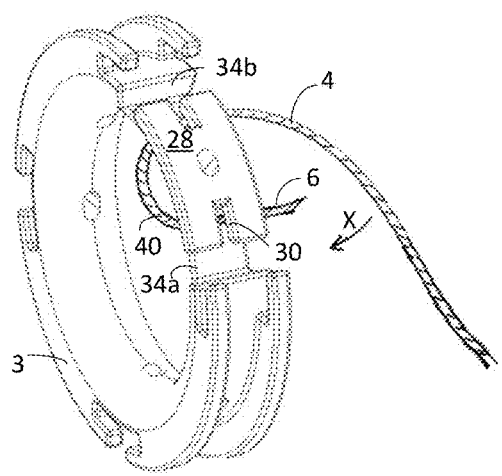
FIGS. 20A-20G show a series of diagrams illustrating by way of example how to attach a length 4 of dental floss to an embodiment of the dental flossing device of the present invention.
Figure 20B:
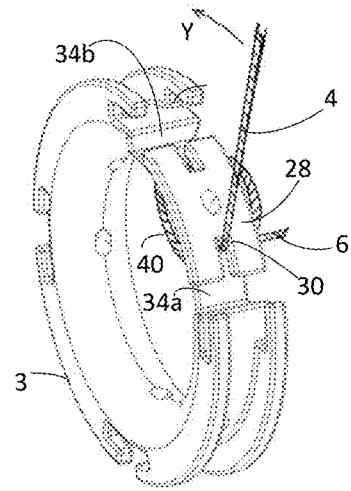
Figure 20C:
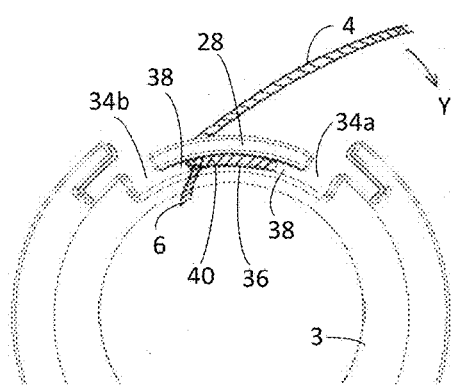

As shown in FIG. 20A, the free end 6 of the length of dental floss 4 is first inserted into the space 38 between the floor 36 of the depression 34a, 34b and the bottom side of the base wall 28. The length of dental floss 4 is then wound around the pedestal 32 that connects the bottom side of the base wall 28 to the floor 36 of the depression 34a, 34b. FIGS. 20C and 20F contain the best views of the pedestal 32, the depression 34a, 34b, the floor 36 and the space 38. As illustrated by FIG. 20A, when the length of dental floss 4 is wrapped around the pedestal 32, it forms one or more loops 40 around the pedestal 32. The one or more loops 40 are thus lodged within the space 38 existing between the bottom surface of the base wall 28 and the top surface of the floor 36 of the depression 34a, 34b. Then the length of dental floss 4 exiting the second end of the depression 34b is moved in the direction X so that it too passes into the first end of the depression 34a where the free end 6 is located. The length of dental floss 4 is then passed through the tines of the niche 30 in the base wall 28 and pulled tight while being guided in the direction Y. See FIGS. 20B and 20C'.

In preferred embodiments, the shape and dimensions of the base wall 28, the pedestal 32 and the depression 34a, 34b are all configured to compress the one or more loops 40 wrapped around the pedestal 32 into the space 38, thereby serving to firmly wedge the one or more loops 40 into the space 38. Ideally, texture is also applied to the pedestal 32, the floor 36 of the depression 34a, 34b, and underside of base wall 28 to increase the amount of friction between the floss and the device and thereby aid in securing the loops 40 of dental floss wedged into the space 38. Moreover, the multiple points of contact between the one or more loops 40 and the sides of the pedestal 32, combined with the multiple points of contact between the tines of the niche 30 and the length of dental floss 4 lodged between the tines of niche 30 also serve to provide additional friction to ensure that the free end 6 and the one or more loops 40 of the length of dental floss 4 will stay secured to the device 3.

Figure 20D:
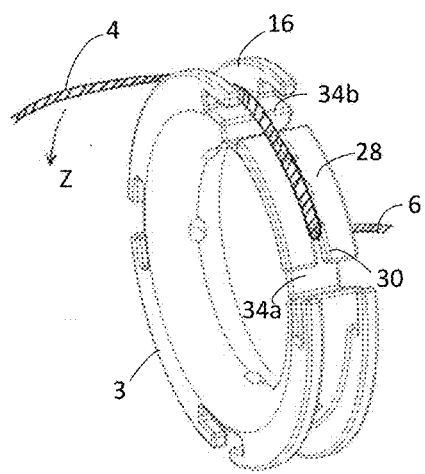
Figure 20E:
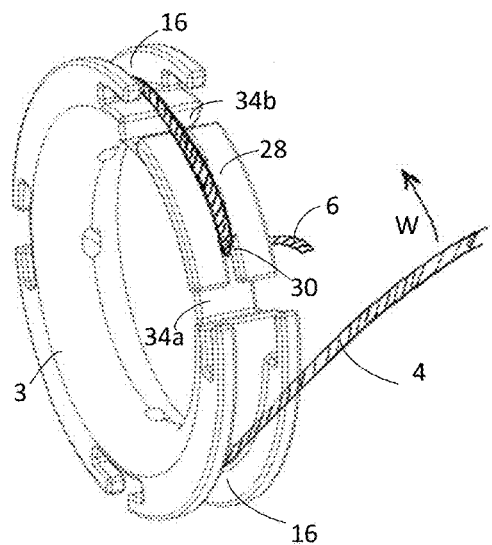
Figure 20F:
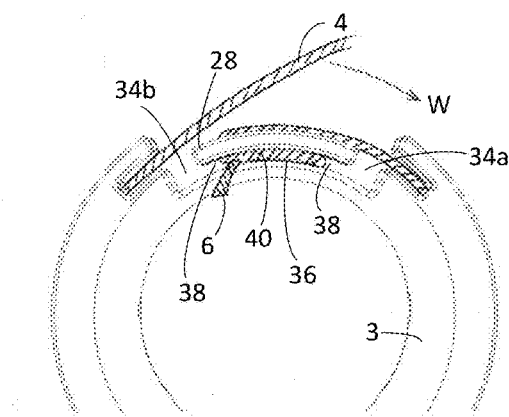
Figure 20G:
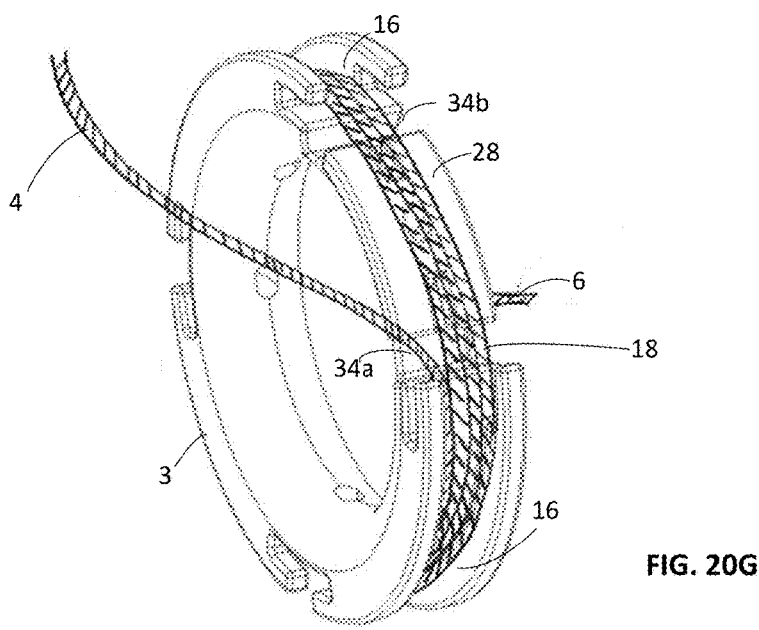

Next, as shown in FIG. 20D, the length of dental floss 4 is moved in the direction Z so that the part of the length of dental floss 4 immediately adjacent to the part passing through the niche 30 will rest against the base wall 28, and the part of the length of dental floss 4 farther away from the niche 30 will pass into the circumferential groove 16. The rest of the length of dental floss 4 is then moved in the direction W (shown in FIGS. 20E and 20F) to wrap the length of dental floss 4 multiple times around the circumferential groove 16 to form the revolutions 18 of dental floss wrapped around the device 3. See FIG. 20G. If the device 3 is to be used as the dispensing ring for the length of dental floss 4, then the desired amount of dental floss (e.g., a two-week supply) is wound into the revolutions 18 inside the circumferential groove 16. This process is repeated to attach the other free end of the dental floss (not shown in FIGS. 20A-20G) to a similar or identical fastener on a companion take-up ring (also not shown), except that the take-up ring does not need to be wound with extra revolutions of dental floss because the purpose of the take-up ring is to receive, collect and store used dental floss during a flossing session.

It is anticipated that some devices configured according to embodiments of the present invention may be made, sold and distributed without the dental floss, which may then be obtained separately. In this case, the dental floss may be cut by using a floss cutter typically provided on the package containing the dental floss or by using any one of a variety of different dental floss cutting devices available on the market. Alternatively, certain embodiments and implementations of the present invention may be pre-packaged and sold with the dental floss, as well as a cutter that is conveniently integrated into the body 8. It is also anticipated that some embodiments of the present invention may include only a single ring (with or without a fresh supply of dental floss), while other embodiments may include two companion rings (as shown in FIGS. 8, 10, 11 and 20), which are packaged and sold together as a kit.

Figure 21:
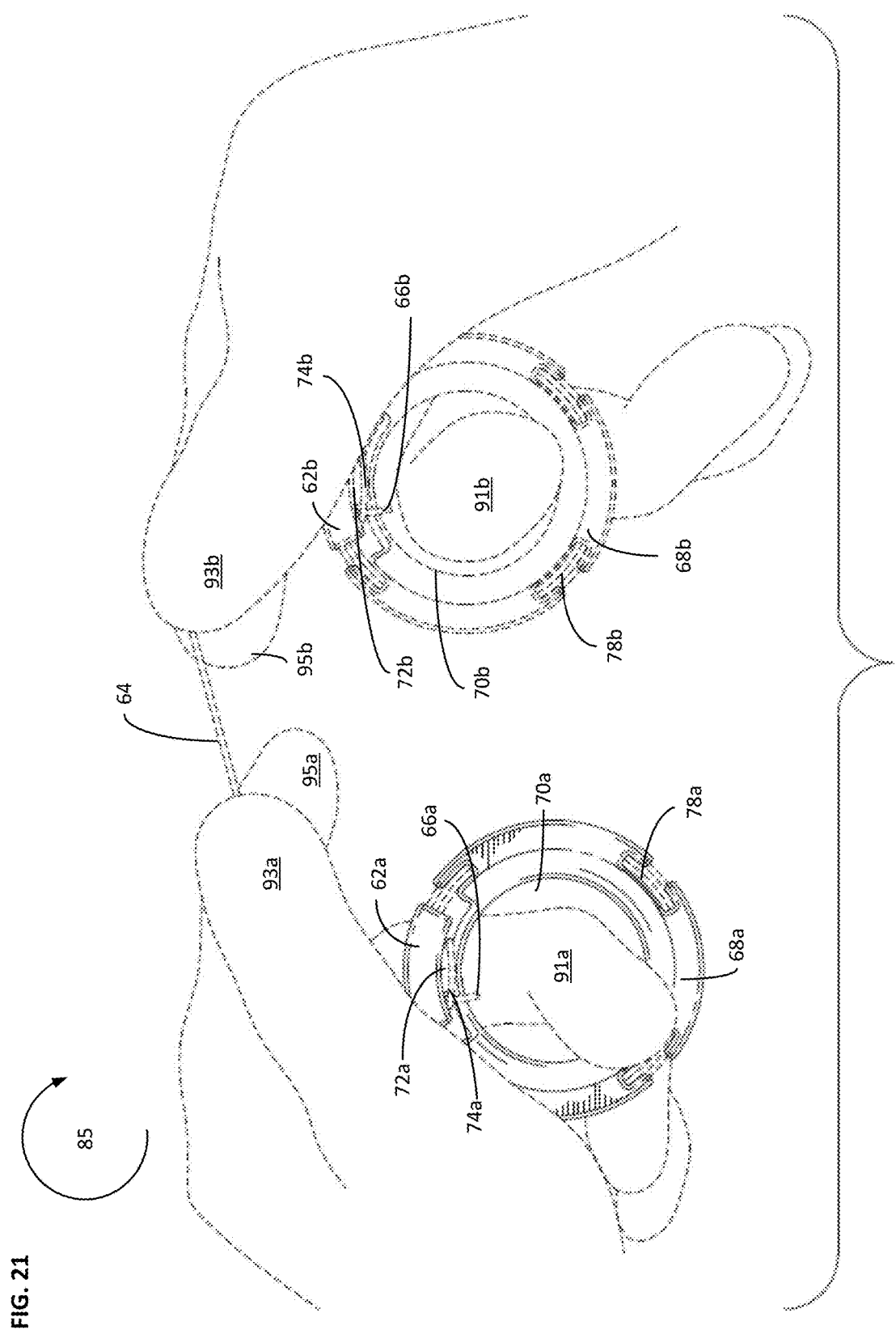
FIG. 21 shows a diagram illustrating by way of example only how the exemplary dental flossing device depicted in FIGS. 7 and 8 might be held in the hands of a user and used in tandem while performing or preparing to perform a flossing operation.

FIG. 21 shows a diagram illustrating by way of example only how the exemplary dental flossing device, like the devices depicted in FIGS. 7 and 8, might be used in tandem and held in the hands of a user while performing or preparing to perform a flossing operation. As shown in FIG. 21, a length of dental floss 64 having free ends 66a and 66b are attached to the fasteners 62a and 62b on two dental flossing rings 68a and 68b in accordance with one exemplary embodiment of the present invention. For purposes of FIG. 21, it is assumed that ring 68a will serve as the dispensing ring for fresh, unused dental floss, and that ring 68b will be used as the take-up ring to take up used and soiled dental floss after it is unwrapped from dispensing ring 68a and used for flossing. It is understood, however, that the roles of the two rings 68a and 68b as dispenser and take-up rings may be reversed, depending on the preference of the user, because the two rings 68a and 68b are identical and symmetric to each other. But assuming ring 68b will serve as the take-up ring, the user first attaches the free end 66a of the length of dental floss 64 to the fastener 62a by wrapping one or more loops 74a of dental floss around the pedestal 72a before passing the floss through the niche (not visible in FIG. 21) in the base wall of the fastener 62a. The other free end 66b of the length of dental floss 64 is attached to the fastener 62b on the take-up ring 68b.

Once the length of dental floss 64 is attached to both rings 68a and 68b, the user then inserts the middle fingers 91a and 91b on each hand through the voids 70a and 70b on the rings 68a and 68b, respectively, or alternatively grips the rings 68a and 68b using fingers, thumbs and palms of both hands without inserting any fingers through the voids 70a and 70b. The thumbs 93a and 93b and index fingers 95a and 95b are used to guide the extended dental floss 64 and manipulate the dental floss 64 into position to perform the actions required for proper flossing. When flossing one section of teeth is complete, the fingers 91a, 91b, 95a, 95b and thumbs 93a and 93b are used to synchronously rotate the rings 68a and 68b in the direction 85 so that fresh, unused dental floss will be unwound from the revolutions 78a of unused dental floss carried by the dispenser ring 68a and the used dental floss will be wound into the revolutions 78b of used dental floss carried by the take-up ring 68b. Thus, the fresh and unused dental floss unwinding from dispenser ring 68a will be moved into position 64 and made ready to be engaged in the next section of teeth to be flossed. The process is repeated until all gaps between the teeth are properly flossed.

Embodiments of the present invention may be manufactured via a variety of manufacturing techniques, depending on requirements, such as turnaround-time, cost, precision and the required level of surface smoothness. Manufacturing options include, but are not limited to, injection molding, plastic machining and 3D printing (described below). If injection molding is used, plastic pellets—rigid when cool but viscous at higher temperatures—are heated to their melting point and then injected into a cavity shaped in the form of the embodiment of the present invention. As the injected plastic cools, it hardens. Plastic machining, however, is the process of whittling plastic down from a larger shape such as disc or torus, like shaving slivers from a branch with a knife until the result is shaped in the form of an embodiment of the present invention. 3D printing (or additive manufacturing) involves making three-dimensional solid objects from a digital file. In an additive process, an embodiment of the present invention may be created by laying down successive layers of material until the entire object is created. Each of these layers can be seen as a thinly sliced horizontal cross-section of the final product. When an embodiment of the present invention requires less than a few hundred parts, the best manufacturing technique will very likely be plastic machining or 3D printing. Otherwise injection molding may be the best option, based on a comparison of the cost of creating the initial mold to the higher expense of machining. Plastic machining may also be a better option if a high degree of precision or uniform surface smoothness are important requirements.

The size, appearance and the dimensions of devices manufactured in accordance with embodiments of the present invention may vary greatly, depending on a variety of factors, including without limitation, the fit and usability for the target customers, the type (or brand) of dental floss to be used with the device, the anticipated amount of dental floss to be stored on the device and aesthetic appeal. While certain parameters, such as the diameter of the void, may be selected in order to achieve a comfortable fit for a typical customer, other parameters, such as the ratio of the void's diameter to the device's overall diameter, or the number and location of the pairs of cleats, may be chosen specifically to create an attractive visual appearance. The inventor of the present invention has determined, for example, that embodiments of the invention having the following dimensions satisfy the above-described functional requirements and also engender a considerable amount of aesthetic appeal. It is understood, however, that other dimensions may be beneficially selected and used without departing from the scope of the claims.

Void Diameter=22.5 mm
Body Diameter=7 mm
Flossing Instrument Diameter 36.5=mm
Circumferential Groove Width=4 mm
Cleat Height=3 mm
Circumferential Groove Width plus Cleat Thickness=7 mm
Cleat Thickness=1.5 mm
Pedestal Height=1.0 mm
Depression Depth=5.5 mm
First Segment Thickness=4 mm
Second Segment Thickness=1.5 mm
Base Side Wall Thickness=1.5 mm
Base Wall Thickness=1.5 mm
Center Point of Notches in First Pair of Cleats=137.5 degrees
Center Point of Notches in Second Pair of Cleat=137.5 degrees
Aeration Holes=0 degrees and 180 degrees
Niche Width=1 mm Hundreds of materials and colors may be used to construct embodiments of the invention, depending on the required characteristics of the final product. For instance, ABS provides toughness, high impact strength and flame-retardant properties. Acetal provides strength with excellent chemical resistance, natural lubrication, dimensional stability and stability at high temperatures. Nylon 6/6 provides strength, rigidity, impact resistance, abrasion resistance, self-lubrication and a high melting point, and is ideal for metal replacement applications. Nylon 6/6 glass fiber provides long-lasting wear and resistance to chemicals, heat, abrasion and impact. Nylon 6/6 glass fiber is also twice as strong as general purpose nylon. PBT (Polybutylene Terephthalate) provides mechanical strength and heat resistance up to 150° C. It is also resistant to solvents and undergoes a minimal amount of shrinking during forming. PC (Polycarbonate) is nearly unbreakable and heat-resistant up to 125° C. with excellent clarity. PC-ABS provides a blend offering rigidity, good impact strength (even in cold temperatures), and dimensional, thermal, and color stability. Polypropylene, which is flexible and lightweight with high tensile strength and very low-density, is inert in acids, alkalis, and solvents. Therefore, it is ideal for hinged parts. Although polystyrene has limited flexibility, it is excellent for molds with fine detail and can be transparent or made to take on various colors. PVC (Polyvinyl Chloride) is durable, flame retardant and chemical resistant, and is available in rigid or flexible forms. TPE (Thermoplastic Elastomers) or TPV (Vulcanizate) have properties that are similar to natural rubber, but are more durable and longer lasting in temperature extremes.

Although the exemplary embodiments, uses and advantages of the invention have been disclosed above with a certain degree of particularity, it will be apparent to those skilled in the art upon consideration of this specification and practice of the invention as disclosed herein that alterations and modifications can be made without departing from the spirit or the scope of the invention, which are intended to be limited only by the following claims and equivalents thereof.

What I claim is:

1. A dental flossing device for use with a length of dental floss having a free end, the dental flossing device comprising:
   a) a first body circumscribing a void adapted to receive one or more fingers of a user, the first body having an outward-facing surface opposite from the void;
   b) at least one pair of cleats, disposed on a first segment of the outward-facing surface, the at least one pair of cleats defining a circumferential groove for receiving and carrying one or more revolutions of said length of dental floss formed by wrapping said length of dental floss along the circumferential groove between the pair of cleats; and
   c) a fastener, disposed on a second segment of said outward-facing surface, the fastener comprising a depression in said outward-facing surface, a crown having a base wall and a niche in the base wall, said fastener further comprising a pedestal that connects the base wall of the crown to a floor of the depression;
   d) wherein the dimensions of the base wall, the niche in the base wall and the pedestal are configured to provide a space between the floor of the depression and the base wall of the crown, the space being of sufficient size to receive and secure a section of the free end of the dental floss wound in a loop about the pedestal before passing through the niche in the base wall;
   e) whereby the base wall, the pedestal, the space between the base wall and the pedestal, the niche and the loop are arranged to secure the section of the free end of the dental floss to the fastener.

2. The dental flossing device of claim 1, wherein:
   a) the pedestal and the base wall are configured to provide a bridge to support a part of said one or more revolutions of dental floss carried by the circumferential groove; and
   b) the loop about the pedestal does not alter or otherwise interfere with the path of the part of said one or more revolutions supported by the bridge.

3. The dental flossing device of claim 2, further comprising a pair of side walls, connected to the base wall of the crown, the pair of sidewalls configured to prevent said part of said one or more revolutions of dental floss passing over the bridge from slipping over the sides of the base wall.

4. The dental flossing device of claim 1, further comprising at least two pairs of cleats disposed on the first segment of the outward-facing surface, the at least two pairs of cleats defining the circumferential groove for receiving and carrying said one or more revolutions of said length of dental floss formed by wrapping said length of dental floss along the circumferential groove between the at least two pairs of cleats.

5. The dental flossing device of claim 1, further comprising at least three pairs of cleats disposed on the first segment of the outward-facing surface, the at least three pairs of cleats defining the circumferential groove for receiving and carrying said one or more revolutions of said length of dental floss formed by wrapping said length of dental floss along the circumferential groove between the at least three pairs of cleats.

6. The dental flossing device of claim 1, wherein a cross section of the first body is substantially circular, or substantially elliptical, or substantially rectangular, or substantially triangular, or a combination of one or more thereof.

7. The dental flossing device of claim 1, wherein a cross section of the void circumscribed by the first body is substantially circular, or substantially elliptical, or substantially rectangular, or substantially triangular, or a combination of one or more thereof.

8. The dental flossing device of claim 1, wherein the length of the surface of the base wall facing the pedestal is larger than the length of the pedestal.

9. The dental flossing device of claim 1, wherein the width of the surface of the base wall facing the pedestal is larger than the width of the pedestal.

10. The dental flossing device of claim 1, wherein a cross sectional area of the base wall of the crown is larger than a cross sectional area of the pedestal.

11. The dental flossing device of claim 1, wherein the niche in the base wall of the crown substantially coincides with a line demarcating the center of the base wall along its primary axis.

12. The dental flossing device of claim 1, further comprising one or more aeration holes extending through the first body from the void to the outward-facing surface.

13. The dental flossing device of claim 1, further comprising:
  a) a second fastener, disposed on a third section of said outward-facing surface, the second fastener comprising a second depression in said outward-facing surface, a second crown having a second base wall and a second niche in the second base wall, said second fastener further comprising a second pedestal that connects the second base wall of the second crown to a floor of the second depression;
  b) wherein the dimensions of the second base wall, the second niche in the second base wall and the second pedestal are configured to provide a second space between the floor of the second depression and the second base wall of the second crown, the second space being of sufficient size to receive and secure the section of the free end of the dental floss wound in a loop around the second pedestal before passing through the second niche in the second base wall;
  c) whereby the second base wall, the second pedestal, the second space between the second base wall and the second pedestal, the second niche and the loop are arranged to secure the section of the free end of the dental floss to the second fastener.

14. The dental flossing device of claim 13, wherein:
  a) the second pedestal and the second base wall are configured to provide a second bridge to support a portion of said one or more revolutions of dental floss carried by the circumferential groove; and)
  b) the support provided by the second bridge permits said portion of said one or more revolutions to pass over the second base wall without coming into contact with the section of the free end wound in a loop about the pedestal.

15. The dental flossing device of claim 14, further comprising a second pair of side walls, connected to the second base wall of the second crown, the second pair of sidewalls configured to prevent said portion of said one or more revolutions of dental floss passing over the second base wall from slipping over the sides of the second base wall.

16. The dental flossing device of claim 1, further comprising:
  a) a notch, located on at least one cleat in said at least one pair of cleats, configured to permit a part of the length of dental floss to pass through the notch at an oblique angle relative to the direction of the wrapping of the revolutions of dental floss carried by the circumferential groove;
  b) whereby, when the part of the length of dental floss passing through the notch at the oblique angle is held under tension by the user, the notch will prevent the revolutions of dental floss carried by the circumferential groove from unwinding or falling out of the circumferential groove.

17. The dental flossing device of claim 16, further comprising a pair of notches, located at opposite ends of each one of said at least one pair of cleats, respectively.

18. The dental flossing device of claim 1, wherein the void circumscribed by said first body is bounded by an inward-facing rectilinear wall opposite the circumferential groove.

19. The dental flossing device of claim 1, wherein the void circumscribed by said first body is bounded by an inward-facing toroidal wall opposite the circumferential groove.

20. The dental flossing device of claim 1, further comprising:
  a) a second body circumscribing a second void adapted to receive one or more fingers from the opposite hand of the user, the second body having a second outward-facing surface opposite from the second void; and
  b) another pair of cleats, disposed on the second outward-facing surface of the second body, defining a second circumferential groove on the second body for taking up and carrying portions of said length of dental floss as said portions of said length of dental floss are unwound and removed from the circumferential groove on the first body.

21. The dental flossing device of claim 20, wherein a cross section of the second body is substantially circular, or substantially elliptical, or substantially rectangular, or substantially triangular, or a combination of one or more thereof.

22. The dental flossing device of claim 20, wherein a cross section of the second void circumscribed by the first body is substantially circular, or substantially elliptical, or substantially rectangular, or substantially triangular, or a combination of one or more thereof.

23. The dental flossing device of claim 20, wherein the shape of said second body is substantially identical to the shape of said first body.

24. The dental flossing device of claim 20, wherein:
  a) said length of dental floss comprises a first free end and second free end;
  b) the first free end of said length of dental floss is secured to the fastener on the first body; and
  c) the second free end of said length of dental floss is secured to a second fastener located on the second body.

25. The dental flossing device of claim 20, wherein the second void circumscribed by said second body is bounded by an inward-facing rectilinear wall opposite the second circumferential groove.

26. The dental flossing device of claim 20, wherein the second void circumscribed by said second body is bounded by an inward-facing toroidal wall opposite the second circumferential groove.

27. The dental flossing device of claim 20, further comprising one or more aeration holes extending through the second body from the second void to the second outward-facing surface.

* * * * *